US010053742B2

(12) United States Patent
Gao et al.

(10) Patent No.: US 10,053,742 B2
(45) Date of Patent: *Aug. 21, 2018

(54) COMPOSITIONS AND METHODS FOR DETECTING HEV NUCLEIC ACID

(71) Applicant: GEN-PROBE INCORPORATED, San Diego, CA (US)

(72) Inventors: Kui Gao, San Diego, CA (US); Edgar O. Ong, San Diego, CA (US); Jennifer Cole, Carlsbad, CA (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 14/911,667

(22) PCT Filed: Aug. 14, 2014

(86) PCT No.: PCT/US2014/051145
§ 371 (c)(1),
(2) Date: Jun. 22, 2016

(87) PCT Pub. No.: WO2015/023892
PCT Pub. Date: Feb. 19, 2015

(65) Prior Publication Data
US 2016/0186272 A1    Jun. 30, 2016

Related U.S. Application Data

(60) Provisional application No. 61/941,303, filed on Feb. 18, 2014, provisional application No. 61/865,848, filed on Aug. 14, 2013.

(51) Int. Cl.
C07H 21/04    (2006.01)
C12Q 1/70    (2006.01)

(52) U.S. Cl.
CPC .................... C12Q 1/707 (2013.01)

(58) Field of Classification Search
None
See application file for complete search history.

(56) References Cited

U.S. PATENT DOCUMENTS

| 5,512,445 | A | 4/1996 | Yang et al. | |
| 6,114,154 | A | 9/2000 | Li | |
| 7,709,626 | B2 * | 5/2010 | Narayanan | C12Q 1/6816 435/6.1 |
| 2003/0149998 | A1 * | 8/2003 | Blatcher | C07K 14/705 800/8 |
| 2012/0016006 | A1 | 1/2012 | Hinkle et al. | |
| 2016/0032412 | A1 * | 2/2016 | Gao | C12Q 1/707 435/5 |

FOREIGN PATENT DOCUMENTS

EP    1400588 A1    3/2004

OTHER PUBLICATIONS

USPTO Office Action, U.S. Appl. No. 14/460,180, dated Jun. 16, 2016.
USPTO Office Action, U.S. Appl. No. 14/460,180, dated Dec. 12, 2016.
USPTO Office Action, U.S. Appl. No. 14/460,180, dated Aug. 9, 2017.
Jeffery Fredman. Are oligonucleotide primers and probes prima facie obvious over larger prior art nucleic acids? Santa Clara Computer & High Technology Law Journal. vol. 19, Issue 1, Article 8. 2003.
Database GenBank, Accession No. AB074918.2 (2008), "Hepatitis E virus genomic RNA, complete genome, isolate: UKN-Sap," 1342-1345.
PCT International Preliminary Report on Patentability, International Application No. PCTUS/2014/051145, dated Feb. 16, 2016.
PCT Written Opinion, International Application No. PCTUS/2014/051145, dated Nov. 11, 2011.
PCT International Search Report, International Application No. PCTUS/2014/051145, dated Nov. 11, 2011.
Enouf et al., "Validation of Single Real-Time TaqMan PCR Assay for the Detection and Quantitation of Four Major Genotypes of Hepatitis E Virus in Clinical Sequence," Journal of Medical Virology, 2006, vol. 78, No. 8, pp. 1076-1082.
Inoue et al., "Developement and validation of an improved RT-PCR assay with nested universal primers for detection of hepatitis E virus strains with significant sequence divergence," Journal of Virological Methods, 2006, vol. 137, No. 2, pp. 325-333.
Narayanan et al., "A broadly reactive one-step real-time RT-PCR assay for rapid and sensitive detection of hepatitis E virus," Journal of Virological Methods, 2006, vol. 131, No. 1, pp. 65-71.
Shukla et al., "Cross-species infections of cultured cells by hepatitis E virus and discovery of an infectious virus-host recombinant," Proceedings of the National Academy of Sciences, 2011, vol. 108, No. 6, pp. 2438-2443.
Shukla et al., "Adaptation of a Genotype 3 Hepatitis E Virus to Efficient Growth in Cell Culture Depends on an Inserted Human Gene Segment Acquired by Recombination," Journal of Virology, 2012, vol. 86, No. 10, pp. 5697-5707.
EPO Communication Pursuant to Article 94(3) EPC, European Patent Application No. 14756196.3, dated Apr. 18, 2017.

(Continued)

Primary Examiner — Michelle S Horning
(74) Attorney, Agent, or Firm — Jeffrey E. Landes; Nicholas V. Sherbina

(57) ABSTRACT

Disclosed are nucleic acid oligomers, including amplification oligomers, capture probes, and detection probes, for detection of Hepatitis E Virus (HEV) nucleic acid. Also disclosed are methods of specific nucleic acid amplification and detection using the disclosed oligomers, as well as corresponding reaction mixtures and kits.

19 Claims, 4 Drawing Sheets

(56) References Cited

OTHER PUBLICATIONS

USPTO Final Office Action, U.S. Appl. No. 14/460,180, dated Dec. 20, 2017.
USPTO Advisory Action, U.S. Appl. No. 14/460,180, dated Mar. 1, 2018.
USPTO Notice of Allowance, U.S. Appl. No. 14/460,180, dated Mar. 29, 2018.
EPO Communication Pursuant to Article 94(3) EPC, European Application No. 14756196.3, dated Apr. 17, 2018.

* cited by examiner

```
GCAGACCACGTATGTGGTCGATGCCATGGAGGCCCATCAGTTCATTAAGG
CTCCTGGCATTACTACTGCCATTGAGCAGGCTGCTCTGGCTGCGGCCAAT
TCCGCCTTGGCGAATGCTGTGGTGGTCCGGCCGTTCTTATCTCGTGTACA
AACTGAGATTCTTATTAATTTGATGCAACCCCGGCAGTTGGTTTTCCGCC
CTGAGGTGCTCTGGAATCACCCTATCCAGCGGGTTATACATAATGAATTG
GAACAGTACTGCCGGGCCCGGGCCGGCCGTTGCCTGGAGGTTGGGGCTCA
CCCGAGGTCCATTAATGACAATCCCAATGTCCTGCACAGGTGCTTTCTTA
GACCGGTTGGCCGAGACGTCCAGCGCTGGTACTCTGCCCCCACCCGTGGC
CCTGCGGCCAACTGCCGCCGCTCCGCGTTGCGTGGTCTCCCTCCCGCTGA
CCGCACTTATTGCTTTGATGGATTCTCCCGCTGTGCTTTTGCTGCAGAGA
CCGGCGTGGCCCTTTACTCTCTGCATGACCTTTGGCCAGCTGATGTCGCA
GAGGCTATGGCCCGCCACGGGATGACACGCCTATATGCTGCACTACACCT
CCCTCCTGAGGTGCTGTTGCCACCCGGCACTTACCACACAACCTCGTATC
TCCTGATCCACGACGGCGACCGTGCCGTCGTAACTTATGAGGGCGATACT
AGTGCAGGCTACAATCACGATGTTTCCATACTTCGTGCGTGGATCCGTAC
TACTAAAATAGTTGGTGACCACCCGTTGGTTATAGAGCGTGTGCGGGCCA
TTGGATGTCATTTTGTGCTGCTGCTCACCGCAGCCCCTGAGCCGTCACCT
ATGCCTTATGTCCCCTACCCTCGTTCAACTGAGGTGTATGTACGATCTAT
ATTTGGCCCTGGTGGCTCCCCATCTTTGTTCCCGTCAGCCTGCTCTACTA
AATCTACTTTTCATGCTGTCCCGGTTCATATCTGGGACCGGCTTATGCTT
TTTGGTGCCACCCTGGACGATCAGGCGTTTTGTTGTTCACGGCTCATGAC
TTACCTCCGTGGTATTAGCTACAAGGTCACTGTCGGTGCGCTTGTTGCTA
ATGAGGGATGGAATGCCTCTGAGGACGCCCTTACTGCAGTGATCACTGCG
GCTTACCTGACTATTTGCCACCAACGCTACCTTCGAACCCAGGCGATATC
CAAGGGTATGCGCCGGTTGGAGGTTGAGCATGCCCAGAAATTCATCACAA
GGCTCTACAGCTGGCTATTTGAGAAATCTGGTCGTGATTATATCCCCGGC
CGCCAGCTTCAGTTCTATGCACAATGTCGGCGGTGGTTATCTGCAGGCTT
CCACCTCGACCCCAGGGTGCTTGTCTTCGATGAAGCAGTGCCATGCCGCT
GTAGGACGTTTTTGAAGAAGGTCGCGGGTAAATTCTGCTGTTTTATGCGG
TGGCTAGGGCAGGAGTGCACCTGTTTCTTGGAGCCAGCTGAGGGCCTAAT
TGGAGACCAAGGCCATGATAATGAGGCCTATGAGGGTTCTGAGGTCGACC
CGGCTGAACCTGCACATCTTGATGTTTCGGGGACCTATGCTGTCCATGGG
CATCAGCTTGAGGCCCTTTATAGGGCACTCAATGTCCCACATGATATTGC
CGCTCGAGCCTCCCGGCTAACGGCTACTGTCGAGCTTGTTGCAAGTCCAG
ACCGCTTAGAGTGCCGTACTGTGCTTGGTAATAAGACCTTTCGGACAACG
GTGGTTGATGGTGCCCATCTTGAAGCAAATGGCCCTGAGGAGTATGTTCT
ATCATTCGACGCCTCTCGTCAGTCTATGGGGGCCGGATCGCACAGCCTCA
```

Figure 1A

```
CATATGAGCTCACCCCTGCTGGTCTGCAGGTCAGGATTTCATCTAATGGC
TTGGATTGTACCGCCGTATTCCCTCCCGGCGGCGCCCCTAGCGCCGCACC
GGGGGAGGTGGCAGCCTTCTGCAGCGCCCTTTATAGATATAACAGGTTCA
CCCAACGGCACTCGCTAACCGGTGGATTATGGTTACACCCTGAGGGGTTG
CTGGGCATCTTCCCCCCTTTCTCTCCTGGACACATCTGGGAGTCTGCTAA
CCCATTTTGTGGGGAGGGGACCTTGTATACCCGAACCTGGTCAACATCTG
GCTTCTCTAGCGACTTCTCCCCCCCTGAGGCGGCCGCCCCTGTTCCGGCT
GCTGCCCCGGGGCTGCCCCACCCCACCCCACCTGTTAGTGACATTTGGGT
GCTGCCACCACCCTCAGAGGAGTCCCAGATCGATGCGGCACCTGTGCCCC
CTGTCCCTAAGACTGTTGGATTGCCTAGCCCCATTGTACTTGCTCCTCCC
TCCCCTCTTCCTTCCCCGTGCGTAAGCCACCATCACCCCGCCTTCTCG
CACTCGTCGTCTCCTCTACACCTATCCTGACGGCGCTAGGGTATATGCGG
GGTCGTTGTTTGAATCAGACTGTGACTGGCTAGTTAACGCCTCAAATCCG
GGCCACCGTCCTGGAGGTGGCCTCTGCCACGCCTTTTACCAACGCTTCCC
AGAGGCGTTTTACCCAACTGAATTCATTATGCGTGAGGGCCTTGCAGCAT
ATACCCTGACCCCGCGCCCTATCATTCATGCAGTGGCTCCCGACTATAGG
GTCGAGCAGAATCCGAAGAGGCTTGAGGCAGCGTACCGGGAAACTTGCTC
CCGTCGCGGCACCGCTGCCTATCCGCTTTTGGGCTCGGGTATATACCAGG
TCCCTGTTAGTCTCAGTTTTGATGCCTGGGAACGCAATCATCGCCCCGGC
GACGAGCTTTACTTGACTGAGCCCGCTGCAGCTTGGTTTGAGGCTAATAA
GCCATCGCAGCCGGCGCTTACTATAACTGAGGACACGGCTCGTACGGCCA
ATCTGGCATTAGAGATTGATGCCGCCACAGAGGTTGGCCGTGCTTGTGCC
GGCTGCACTATCAGCCCGGGGGTTGTGCATTACCAGTTTACTGCCGGGGT
CCCGGGCTCGGGCAAGTCAAGGTCCATACAACAGGGAGACGTCGATGTGG
TGGTTGTGCCCACCCGGGAGCTTCGTAATAGTTGGCGCCGCCGGGGTTTT
GCGGCTTTCACACCTCACACAGCGGCCCGTGTTACTATTGGTCGCCGCGT
TGTGATTGATGAGGCTCCGTCCCTCCCGCCGCACTTGCTGCTGCTACACA
TGCAACGGGCCTCCTCGGTCCATCTCCTCGGCGACCCAAATCAGATTCCT
GCTATTGATTTTGAACATGCCGGCCTGGTCCCCGCGATCCGTCCCGAGCT
TGCACCAACGAGCTGGTGGCATGTTACACACCGCTGCCCGGCAGATGTGT
GTGAGCTTATACGTGGGGCCTACCCTAAGATCCAGACCACGAGTCGTGTG
CTACGGTCCCTGTTTTGGAACGAACCGGCCATTGGCCAGAAGCTGGTTTT
CACGCAGGCTGCTAAGGCTGCTAATCCTGGTGCGATCACGGTTCATGAGG
CTCAGGGTGCCACCTTCACGGAGACCACAATCATAGCCACGGCTGATGCT
AGGGGCCTTATTCAGTCATCCCGAGCTCACGCTATAGTCGCACTCACCCG
CCACACTGAGAAGTGTGTTATTTTAGATGCCCCGGCCTACTGCGCGAGG
TCGGTATTTCAGATGTGATTGTCAATAACTTTTTCCTTGCTGGTGGAGAG
```

Figure 1B

```
GTTGGCCACCACCGCCCCTCCGTGATACCTCGCGGTAACCCCGATCAGAA
TCTCGGGACTCTACAGGCATTCCCGCCGTCTTGCCAGATTAGTGCCTACC
ACCAGTTGGCTGAGGAATTAGGCCACCGCCCAGCTCCTGTCGCCGCCGTC
TTACCCCCTTGCCCGGAGCTTGAGCAGGGCCTGCTCTACATGCCACAAGA
GCTTACTGTGTCCGATAGTGTGTTGGTATTTGAACTCACAGATATAGTCC
ATTGCCGTATGGCCGCTCCAAGCCAGCGAAAGGCTGTTCTCTCAACACTT
GTCGGGAGGTATGGCCGTAGAACGAAATTATATGAGGCGGCACATTCAGA
TGTTCGTGAGTCCCTAGCTAGGTTCATCCCCACTATCGGGCCTGTTCAGG
CCACCACATGTGAGTTGTATGAGTTGGTTGAGGCCATGGTGGAGAAGGGT
CAGGACGGCTCTGCCGTCCTAGAGCTTGACCTTTGCAATCGTGACGTCTC
GCGTATCACATTTTTCCAAAAGGATTGCAATAAATTCACAACTGGTGAGA
CTATTGCCCATGGCAAGGTTGGCCAGGGTATATCGGCCTGGAGTAAGACC
TTCTGTGCCCTGTTTGGCCCGTGGTTCCGCGCTATAGAAAAGAGATATT
GGCCCTGCTCCCGCCTAATATCTTTTATGGCGACGCTTATGAAGAGTCAG
TGTTTGCTGCCGCTGTGTCTGGGCGGGGTCATGTATGGTATTTGAAAAT
GATTTTTCGGAATTTGACAGTACTCAGAACAACTTCTCTCGGCCTTGA
GTGTGTGGTCATGGAGGAGTGCGGCATGCCCCAGTGGTTGATTAGGTTGT
ACCATCTGGTTCGGTCAGCCTGGATTTTGCAGGCGCCGAAGGAGTCTCTT
AAGGGTTTTTGGAAGAAGCACTCTGGTGAGCCTGGTACCCTTCTCTGGAA
CACCGTCTGGAACATGGCGATTATAGCGCACTGTTACGAGTTCCGTGACT
TTCGCGTTGCCGCCTTCAAGGGTGATGATTCGGTGGTCCTTTGCAGCGAC
TATCGGCAGAGCCGCAATGCGGCTGCCTTAATTGCAGGCTGTGGGCTCAA
ATTGAAGGTCGATTATCGTCCTATTGGGCTGTATGCTGGGGTGGTGGTGG
CCCCTGGTTTGGGGACACTGCCCGACGTGGTGCGTTTTGCTGGTCGGTTG
TCTGAAAAGAATTGGGGCCCCGGCCCTGAACGTGCTGAGCAGCTGCGTCT
CGCTGTTTGTGATTTCCTTCGAGGGTTGACGAATGTTGCGCAGGTTTGTG
TTGATGTTGTGTCCCGTGTTTACGGAGTCAGCCCCGGGCTGGTACATAAC
CTTATTGGCATGCTGCAGACCATTGCCGATGGCAAGGCTCACTTCACAGA
GACCATTAAACCTGTGCTTGACCTTACGAATTCCATCATACAGCGGGAAG
AATGAATAACATGTCTTTTGCATCGCCCATGGGATCACCATGCGCCCTAG
GGCTGTTCTGTTGTTGTTCCTCGTGCTTTTGCCTATGCTGCCCGCGCCAC
CGGCCGGTCAGCCGTCTGGCCGTCGCCGTGGGCGGCGCAGCGGCGGTGCC
GGCGGTGGTTTCTGGGGTGACAGGGTTGATTCTCAGCCCTTCGCCCTCCC
CTATATTCATCCAACCAACCCCTTCGCCGCCGATGTCGTTTCACAACCCG
GGGCTGGAACTCGCCCTCGACAGCCGCCCCGCCCCCTTGGCTCCGCTTGG
CGTGACCAGTCCCAGCGCCCCTCCGCTGCCCCCCGCCGTCGATCTGCCCC
AGCTGGGGCTGCGCCGTTGACCGCTGTATCACCGGCTCCTGACACAGCCC
```

Figure 1C

```
CTGTGCCTGATGTTGATTCACGCGGTGCTATCCTGCGCCGGCAGTACAAT
CTGTCCACGTCCCCGCTCACGTCATCTGTCGCCTCGGGCACAAATCTGGT
TCTCTATGCTGCCCGCTTAATCCTCTCCTGCCCCTTCAGGATGGCACCA
ACACTCATATTATGGCCACTGAGGCATCCAATTATGCCCAGTATCGGGTT
GTTCGAGCTACGATCCGTTATCGCCCGTTGGTGCCGAATGCAGTTGGCGG
TTATGCTATTTCTATTTCTTTTTGGCCTCAAACCACAACTACTCCCACCT
CTGTCGACATGAATTCTATCACTTCCACTGATGTTAGGATTTTGGTTCAG
CCCGGCATTGCCTCCGAGTTAGTCATCCCTAGTGAGCGCCTCCACTACCG
CAATCAAGGCTGGCGCTCTGTTGAGACCACGGGTGTGGCCGAGGAGGAGG
CTACTTCCGGTCTGGTAATGCTTTGTATTCATGGCTCTCCTGTTAATTCC
TACACTAATACACCTTATACTGGTGCACTGGGGCTCCTTGATTTTGCATT
AGAGCTTGAATTTAGAAATCTGACACCCGGGAACACAAACACCCGTGTTT
CCCGGTATACCAGCACAGCCCGTCACCGGCTGCGCCGCGGTGCTGATGGG
ACTGCTGAGCTTACCACCACAGCAGCCACACGTTTCATGAAGGATTTACA
TTTTACTGGCACGAATGGTGTTGGTGAGGTGGGTCGTGGCATCGCTCTGA
CATTGTTTAATCTCGCTGACACGCTTCTCGGTGGTTTACCGACAGAATTG
ATTTCGTCGGCCGGGGGTCAACTGTTTTACTCCCGCCCTGTTGTCTCGGC
CAATGGCGAGCCAACAGTAAAGTTATACACATCTGTTGAGAATGCGCAGC
AAGATAAGGGCATTACCATCCCACACGATATAGATCTGGGTGACTCCCGT
GTGGTTATTCAGGATTATGATAACCAGCACGAGCAAGATCGGCCTACTCC
GTCACCTGCCCCCTCCCGCCCTTTCTCAGTTCTTCGTGCTAATGATGTTC
TGTGGCTCTCCCTCACCGCCGCTGAGTATGACCAGACTACGTATGGGTCG
TCCACCAACCCTATGTATGTCTCCGACACAGTCACGCTCGTTAATGTGGC
CACTGGAGCCCAGGCTGTGGCCCGCTCTCTTGATTGGTCTAAAGTTACCT
TGGATGGCCGCCCCCTTACTACCATTCAGCAGTATTCTAAGACATTCTAT
GTCCTTCCGCTCCGCGGGAAGCTGTCTTTCTGGGAGGCTGGTACGACTAA
GGCCGGTTACCCGTATAATTATAATACTACTGCTAGTGATCAGATCTTGA
TTGAGAACGCGGCCGGCCACCGTGTCGCTATTTCTACCTATACTACTAGC
TTGGGTGCCGGCCCTACCTCGATCTCTGCGGTCGGTGTACTAGCTCCACA
TTCGGCCCTCGCCGTTCTAGAGGACACCGTTGATTACCCCGCCCGCGCTC
ACACTTTTGATGATTTCTGCCCGGAGTGCCGTACCCTCGGTTTGCAGGGT
TGTGCATTCCAGTCTACTATCGCTGAGCTTCAGCGTCTTAAAATGAAGGT
AGGTAAAACCCGGGAGTCTTAATTAATTCCTTTTGTGCCCCCTTCGCAGC
TTTCTCTGGCTTTATTTCTTATTTCTGCTTTTCGCGCTCCCTGGAAAAAA
AAAAAA
```

Figure 1D

COMPOSITIONS AND METHODS FOR DETECTING HEV NUCLEIC ACID

RELATED APPLICATIONS

This application is a National Stage entry from PCT application PCT/US14/51145, filed Aug. 14, 2014, which claims the benefit under 35 U.S.C. § 119(e) of provisional application No. 61/865,848, filed Aug. 14, 2013, and of provisional application 61/941,303, filed Feb. 18, 2014, the entire contents of each of which is incorporated herein by reference in their entirety.

BACKGROUND OF THE INVENTION

Hepatitis E Virus (HEV) is a single-stranded, positive-sense RNA virus classified in the family Hepeviridae and the sole member of the genus *Hepevirus*, of which mammalian HEV and avian HEV are the two major known species. Dalton et al., *Lancet Infect. Dis.* 8:698-709, 2008; Baylis et al., *J. Clin. Microbiol.* 49:1234-1239, 2011. Mammalian HEV, having a reservoir in pigs and potentially other mammals, is a major cause of acute hepatitis in humans. See Dalton et al., supra. The virus is transmitted primarily via the fecal-oral route and is associated with sporadic infections and epidemics in developing countries, particularly in areas with poor sanitation and weak public health infrastructures. In developed countries, HEV infection has been considered rare, occurring primarily in individuals infected while traveling to regions where the virus is endemic. Recently, however, autochthonous infections are being reported more frequently in developed regions, including North America, Europe, Japan, New Zealand, and Australia. Autochthonous hepatitis E in developed countries is, therefore, more common than previously recognized, and may be more common than hepatitis A. Dalton et al., *Lancet Infect. Dis.* 8:698-709, 2008.

Four major genotypes of HEV are known to cause infections in humans. Baylis et al., supra. Clinical features of HEV infection can include mild to severe hepatitis as well as subacute liver failure. See, e.g., Pina et al., *J. Hepatol.* 33:826-833, 2000; Sainokami et al., *J. Gastroenterol.* 39:640-648, 2004; Tsang et al., *Clin. Infect. Dis.* 30:618-619, 2000; Widdowson et al., *Clin. Infect. Dis.* 36:29-33, 2003; Dalton et al., *Eur. J. Gastroenterol. Hepatol.* 20:784-790, 2008. HEV infection has a poor prognosis in pregnant women, as well as individuals having pre-existing chronic liver disease. See Borkakoti et al., *J. Med. Virol.* 85:620-626, 2013; Baylis et al., supra. Diagnostic testing for HEV in patients with hepatitis symptoms is important, particularly for patients in which other causes of acute hepatitis have been excluded. See Baylis et al., supra; Waar et al., *J. Clin. Virol.* 33:145-149, 2005.

Accordingly, there is a need for compositions, kits, and methods for detecting the presence or absence of HEV in a specimen with high specificity and sensitivity. Such compositions, kits, and methods would be particularly useful for the diagnosis of HEV, for the screening and/or monitoring of the presence of HEV in a blood or plasma donation, or for monitoring a patient's response to treatment. The present invention meets these and other needs.

SUMMARY OF THE INVENTION

In one aspect, the present invention provides a combination of at least two oligomers for determining the presence or absence of hepatitis E virus (HEV) in a sample. The oligomer combination includes at least two amplification oligomers for amplifying complementary nucleic acid strands of a target region of an HEV target nucleic acid, where (a) at least one amplification oligomer is selected from (i) an oligomer comprising a target-hybridizing sequence that is from about 14 to about 23 contiguous nucleotides contained in the sequence of SEQ ID NO:63 and that includes at least the sequence of SEQ ID NO:26, including RNA equivalents and DNA/RNA chimerics thereof, and (ii) an oligomer comprising a target-hybridizing sequence that is from about 14 to about 23 contiguous nucleotides contained in the sequence of SEQ ID NO:16, including RNA equivalents and DNA/RNA chimerics thereof; and (b) at least one amplification oligomer comprises a target-hybridizing sequence that is from about 17 to about 28 contiguous nucleotides contained in the sequence of SEQ ID NO:47 and that includes at least the sequence of SEQ ID NO:25, including RNA equivalents and DNA/RNA chimerics thereof.

Suitable amplification oligomers as specified above in (a) include oligomers comprising a target-hybridizing sequence selected from SEQ ID NO:29, SEQ ID NO:30, SEQ ID NO:31, SEQ ID NO:32, SEQ ID NO:33, SEQ ID NO:34, SEQ ID NO:35, SEQ ID NO:52, SEQ ID NO:53, SEQ ID NO:54, SEQ ID NO:61, SEQ ID NO:62, SEQ ID NO:64, SEQ ID NO:65, and SEQ ID NO:66, including RNA equivalents and DNA/RNA chimerics thereof. In some preferred variations, an amplification oligomer of (a) comprises a target-hybridizing sequence selected from SEQ ID NO:29, SEQ ID NO:31, SEQ ID NO:32, SEQ ID NO:33, SEQ ID NO:34, SEQ ID NO:35, SEQ ID NO:61, SEQ ID NO:62, SEQ ID NO:64, SEQ ID NO:65, and SEQ ID NO:66, including RNA equivalents and DNA/RNA chimerics thereof. In some embodiments, an amplification oligomer of (a) comprises a target-hybridizing sequence that is from about 14 to about 20 nucleotides contained in the sequence of SEQ ID NO:13 (e.g., SEQ ID NO:33, SEQ ID NO:34, SEQ ID NO:35, SEQ ID NO:62, SEQ ID NO:64, SEQ ID NO:65, or SEQ ID NO:66).

In certain variations, an amplification oligomer as specified in (a) comprises a target-hybridizing sequence that is from 15 to 17 nucleotides contained in the sequence of SEQ ID NO:16 and that includes at least the sequence of SEQ ID NO:27, including RNA equivalents and DNA/RNA chimerics thereof (e.g., a target-hybridizing sequence selected from SEQ ID NO:29, SEQ ID NO:30, SEQ ID NO:31, and SEQ ID NO:32, including RNA equivalents and DNA/RNA chimerics thereof). In some embodiments, an amplification oligomer of (a) comprises a target-hybridizing sequence of SEQ ID NO:28, including RNA equivalents and DNA/RNA chimerics thereof (e.g., a target-hybridizing sequence selected from SEQ ID NO:29 and SEQ ID NO:32, including RNA equivalents and DNA/RNA chimerics thereof).

Suitable amplification oligomers as specified above in (b) include oligomers comprising a target-hybridizing sequence selected from SEQ ID NO:21, SEQ ID NO:22, SEQ ID NO:23, SEQ ID NO:24, SEQ ID NO:45, SEQ ID NO:46, SEQ ID NO:48, SEQ ID NO:49, SEQ ID NO:50, SEQ ID NO:51, and SEQ ID NO:56, including RNA equivalents and DNA/RNA chimerics thereof. In some preferred variations, an amplification oligomer of (b) comprises a target-hybridizing sequence selected from SEQ ID NO:24 and SEQ ID NO:56, including RNA equivalents and DNA/RNA chimerics thereof. In other preferred variations, an amplification oligomer of (b) comprises a target-hybridizing sequence selected from SEQ ID NO:22, SEQ ID NO:23, SEQ ID NO:45, SEQ ID NO:46, and SEQ ID NO:51, including RNA equivalents and DNA/RNA chimerics thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

In some embodiments, a combination of at least two oligomers as above includes an amplification oligomer as specified in (a)(i) and an amplification oligomer as specified in (a)(ii). In some such embodiments, the amplification oligomer of (a)(i) comprises a target-hybridizing sequence selected from SEQ ID NO:33, SEQ ID NO:34, SEQ ID NO:35, SEQ ID NO:61, SEQ ID NO:62, SEQ ID NO:64, SEQ ID NO:65, and SEQ ID NO:66, including RNA equivalents and DNA/RNA chimerics thereof. In certain preferred variations, the amplification oligomer of (a)(i) comprises a target-hybridizing sequence selected from SEQ ID NO:62, SEQ ID NO:64, SEQ ID NO:65, and SEQ ID NO:66, including RNA equivalents and DNA/RNA chimerics thereof.

In certain embodiments comprising an amplification oligomer as specified in (a)(i) and an amplification oligomer as specified in (a)(ii), the amplification oligomer of (a)(ii) comprises a target-hybridizing sequence selected from SEQ ID NO:29, SEQ ID NO:30, SEQ ID NO:31, SEQ ID NO:32, SEQ ID NO:52, SEQ ID NO:53, and SEQ ID NO:54, including RNA equivalents and DNA/RNA chimerics thereof. In certain preferred variations, the amplification oligomer of (a)(ii) comprises a target-hybridizing sequence selected from SEQ ID NO:29, SEQ ID NO:31, and SEQ ID NO:32, including RNA equivalents and DNA/RNA chimerics thereof. In particular variations, (I) the amplification oligomer of (a)(i) comprises the target-hybridizing sequence of SEQ ID NO:64, or an RNA equivalent or DNA/RNA chimeric thereof, and the amplification oligomer of (a)(ii) comprises the target-hybridizing sequence of SEQ ID NO:29, or an RNA equivalent or DNA/RNA chimeric thereof; or (II) the amplification oligomer of (a)(i) comprises the target-hybridizing sequence of SEQ ID NO:65, or an RNA equivalent or DNA/RNA chimeric thereof, and the amplification oligomer of (a)(ii) comprises the target-hybridizing sequence of SEQ ID NO:29 or SEQ ID NO:31, or an RNA equivalent or DNA/RNA chimeric thereof.

In some embodiments, a combination of at least two oligomers as above includes a first amplification oligomer as specified in (a)(ii) and a second amplification oligomer as specified in (a)(ii). In some such embodiments, each of the first and second amplification oligomer as in (a)(ii) comprises a target-hybridizing sequence that is from 15 to 17 nucleotides contained in the sequence of SEQ ID NO:16 and that includes at least the sequence of SEQ ID NO:27, including RNA equivalents and DNA/RNA chimerics thereof (e.g., a target-hybridizing sequence selected from SEQ ID NO:29, SEQ ID NO:30, SEQ ID NO:31, and SEQ ID NO:32, including RNA equivalents and DNA/RNA chimerics thereof). In certain variations, each of the first and second amplification oligomers of (a)(ii) comprises a target-hybridizing sequence of SEQ ID NO:28, including RNA equivalents and DNA/RNA chimerics thereof. In a particular variations, the first amplification oligomer of (a)(ii) comprises the target hybridizing sequence of SEQ ID NO:29, or an RNA equivalent or DNA/RNA chimeric thereof, and the second amplification oligomer of (a)(ii) comprises the target hybridizing sequence of SEQ ID NO:32, or an RNA equivalent or DNA/RNA chimeric thereof.

In some embodiments of an oligomer combination as above, the combination includes first and second amplification oligomers as specified in (b). In some such embodiments, the first amplification oligomer of (b) comprises a target-hybridizing sequence selected from SEQ ID NO:24 and SEQ ID NO:56, including RNA equivalents and DNA/RNA chimerics thereof. In other embodiments, the first amplification oligomer of (b) comprises a target-hybridizing sequence selected from SEQ ID NO:22, SEQ ID NO:23, SEQ ID NO:45, SEQ ID NO:46, and SEQ ID NO:51, including RNA equivalents and DNA/RNA chimerics thereof. In particular variations, (I) the first amplification oligomer of (b) comprises the target-hybridizing sequence of SEQ ID NO:24, or an RNA equivalent or DNA/RNA chimeric thereof, and the second amplification oligomer of (b) comprises the target-hybridizing sequence of SEQ ID NO:56, or an RNA equivalent or DNA/RNA chimeric thereof; or (II) the first amplification oligomer of (b) comprises the target-hybridizing sequence of SEQ ID NO:23 or SEQ ID NO:51, or an RNA equivalent or DNA/RNA chimeric thereof, and the second amplification oligomer of (b) comprises the target-hybridizing sequence of SEQ ID NO:45, or an RNA equivalent or DNA/RNA chimeric thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

An oligomer combination as above may include an amplification oligomer as in (a)(i), an amplification oligomer as in (a)(ii), a first amplification oligomer as in (b), and a second amplification oligomer as in (b). In a particular variation, the amplification oligomer of (a)(i) comprises the target-hybridizing sequence of SEQ ID NO:64, or an RNA equivalent or DNA/RNA chimeric thereof; the amplification oligomer of (a)(ii) comprises the target-hybridizing sequence of SEQ ID NO:29, or an RNA equivalent or DNA/RNA chimeric thereof; the first amplification oligomer of (b) comprises the target-hybridizing sequence of SEQ ID NO:24, or an RNA equivalent or DNA/RNA chimeric thereof; and the second amplification oligomer of (b) comprises the target-hybridizing sequence of SEQ ID NO:56, or an RNA equivalent or DNA/RNA chimeric thereof. In another variation, the amplification oligomer of (a)(i) comprises the target-hybridizing sequence of SEQ ID NO:29, or an RNA equivalent or DNA/RNA chimeric thereof; the amplification oligomer of (a)(ii) comprises the target-hybridizing sequence of SEQ ID NO:65; or an RNA equivalent or DNA/RNA chimeric thereof, the first amplification oligomer of (b) comprises the target-hybridizing sequence of SEQ ID NO:24; or an RNA equivalent or DNA/RNA chimeric thereof; and the second amplification oligomer of (b) comprises the target-hybridizing sequence of SEQ ID NO:56, or an RNA equivalent or DNA/RNA chimeric thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

An oligomer combination as above may include a first amplification oligomer as in (a)(ii), a second amplification oligomer as in (a)(ii), a first amplification oligomer as in (b), and a second amplification oligomer as in (b). In a particular variation, the first amplification oligomer of (a)(ii) comprises the target-hybridizing sequence of SEQ ID NO:29, or an RNA equivalent or DNA/RNA chimeric thereof; the second amplification oligomer of (a)(ii) comprises the target-hybridizing sequence of SEQ ID NO:32, or an RNA equivalent or DNA/RNA chimeric thereof; the first amplification oligomer of (b) comprises the target-hybridizing sequence of SEQ ID NO:24, or an RNA equivalent or DNA/RNA chimeric thereof; and the second amplification oligomer of (b) comprises the target-hybridizing sequence of SEQ ID NO:46, or an RNA equivalent or DNA/RNA chimeric thereof.

In yet other embodiments of an oligomer combination as above, an amplification oligomer of (a) comprises a target-hybridizing sequence selected from SEQ ID NO:29, SEQ ID NO:62, SEQ ID NO:64, SEQ ID NO:65, and SEQ ID NO:66, including RNA equivalents and DNA/RNA chimerics thereof, and an amplification oligomer of (b) comprises a target-hybridizing sequence selected from SEQ ID NO:24 and SEQ ID NO:56, including RNA equivalents and DNA/RNA chimerics thereof. In some such embodiments, the combination includes a set of first, second, and third amplification oligomers comprising a set of first, second, and third target-hybridizing sequences, respectively, where the set of target-hybridizing sequences is selected from sets (i)-(vi) as follows: (i) SEQ ID NO:65, SEQ ID NO:29, and SEQ ID NO:24, including RNA equivalents and DNA/RNA chimerics thereof; (ii) SEQ ID NO:65, SEQ ID NO:29, and SEQ ID NO:56, including RNA equivalents and DNA/RNA chimerics thereof; (iii) SEQ ID NO:29, SEQ ID NO:24, and SEQ ID NO:56, including RNA equivalents and DNA/RNA chimerics thereof; (iv) SEQ ID NO:66, SEQ ID NO:24, and SEQ ID NO:56, including RNA equivalents and DNA/RNA chimerics thereof; (v) SEQ ID NO:65, SEQ ID NO:24, and SEQ ID NO:56, including RNA equivalents and DNA/RNA chimerics thereof; and (vi) SEQ ID NO:62, SEQ ID NO:29, and SEQ ID NO:56, including RNA equivalents and DNA/RNA chimerics thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

In some embodiments, an oligomer combination as above includes a set of first and second amplification oligomers comprising a set of first (A) and second (B) target-hybridizing sequences, respectively, where the set of target-hybridizing sequences is selected from sets (i)-(xiv) as follows:
  (i) (A) SEQ ID NO:54, including RNA equivalents and DNA/RNA chimerics thereof, and
      (B) SEQ ID NO:21, 22, 23, 24, 45, 56, or 51, or an RNA equivalent or DNA/RNA chimeric thereof;
  (ii) (A) SEQ ID NO:53, including RNA equivalents and DNA/RNA chimerics thereof, and
      (B) SEQ ID NO:23, 24, 45, 56, or 51, or an RNA equivalent or DNA/RNA chimeric thereof;
  (iii) (A) SEQ ID NO:52, or an RNA equivalent or DNA/RNA chimeric thereof, and
      (B) SEQ ID NO:24, or an RNA equivalent or DNA/RNA chimeric thereof;
  (iv) (A) SEQ ID NO:31, or an RNA equivalent or DNA/RNA chimeric thereof, and
      (B) SEQ ID NOs:21, 22, 23, 24, 45, 56, 48, 49, 50, or 51, or an RNA equivalent or DNA/RNA chimeric thereof;
  (v) (A) SEQ ID NO:30, or an RNA equivalent or DNA/RNA chimeric thereof, and
      (B) SEQ ID NO:21, 22, 23, 24, 45, 56, 50, or 51, or an RNA equivalent or DNA/RNA chimeric thereof;
  (vi) (A) SEQ ID NO:29, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (vii) (A) SEQ ID NO:66, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (viii) (A) SEQ ID NO:65, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (ix) (A) SEQ ID NO:64, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (x) (A) SEQ ID NO:62, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (xi) (A) SEQ ID NO:35, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (xii) (A) SEQ ID NO:34, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof;
  (xiii) (A) SEQ ID NO:33, or an RNA equivalent or DNA/RNA chimeric thereof, and
      (B) SEQ ID NO:21, 22, 23, 24, 41, 52, 44, 45, 46, or 47, or an RNA equivalent or DNA/RNA chimeric thereof; and
  (xiv) (A) SEQ ID NO:61, or an RNA equivalent or DNA/RNA chimeric thereof, and
      (B) SEQ ID NO:21, 22, 23, 24, 45, 56, 48, 49, 50, or 51, or an RNA equivalent or DNA/RNA chimeric thereof.

In certain embodiments comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof). In particular variations, the set of target-hybridizing sequences A and B is selected from sets (i)-(xiii) as follows:
  (i) (A) SEQ ID NO:54, or an RNA equivalent or DNA/RNA chimeric thereof, and
      (B) SEQ ID NO:24, or an RNA equivalent or DNA/RNA chimeric thereof;
  (ii) (A) SEQ ID NO:53, or an RNA equivalent or DNA/RNA chimeric thereof, and
      (B) SEQ ID NO:45, or an RNA equivalent or DNA/RNA chimeric thereof;
  (iii) (A) SEQ ID NO:31, or an RNA equivalent or DNA/RNA chimeric thereof, and
      (B) SEQ ID NO:22, 45, 49, 50, or 51, or an RNA equivalent or DNA/RNA chimeric thereof;
  (iv) (A) SEQ ID NO:30, or an RNA equivalent or DNA/RNA chimeric thereof, and
      (B) SEQ ID NO:56, or an RNA equivalent or DNA/RNA chimeric thereof;

(v) (A) SEQ ID NO:29, or an RNA equivalent or DNA/RNA chimeric thereof, and
(B) SEQ ID NO:21, 56, 48, 50, or 51, or an RNA equivalent or DNA/RNA chimeric thereof;
(vi) (A) SEQ ID NO:66, or an RNA equivalent or DNA/RNA chimeric thereof, and
(B) SEQ ID NO:22, 23, 45, 56, or 51, or an RNA equivalent or DNA/RNA chimeric thereof;
(vii) (A) SEQ ID NO:65, or an RNA equivalent or DNA/RNA chimeric thereof, and
(B) SEQ ID NO:23, 45, 56, or 51, or an RNA equivalent or DNA/RNA chimeric thereof;
(viii) (A) SEQ ID NO:64, or an RNA equivalent or DNA/RNA chimeric thereof, and
(B) SEQ ID NO:22, 24, 45, 56, or 50, or an RNA equivalent or DNA/RNA chimeric thereof;
(ix) (A) SEQ ID NO:62, or an RNA equivalent or DNA/RNA chimeric thereof, and
(B) SEQ ID NO:22, 23, 24, 45, or 56, or an RNA equivalent or DNA/RNA chimeric thereof;
(x) (A) SEQ ID NO:35, or an RNA equivalent or DNA/RNA chimeric thereof, and
(B) SEQ ID NO:23, 45, or 56, or an RNA equivalent or DNA/RNA chimeric thereof;
(xi) (A) SEQ ID NO:34, or an RNA equivalent or DNA/RNA chimeric thereof, and
(B) SEQ ID NO:23, 45, or 56, or an RNA equivalent or DNA/RNA chimeric thereof;
(xii) (A) SEQ ID NO:33, or an RNA equivalent or DNA/RNA chimeric thereof, and
(B) SEQ ID NO:23, 45, or 56, or an RNA equivalent or DNA/RNA chimeric thereof; and
(xiii) (A) SEQ ID NO:61, or an RNA equivalent or DNA/RNA chimeric thereof, and
(B) SEQ ID NO:22, 45, or 56, or an RNA equivalent or DNA/RNA chimeric thereof.

In still other embodiments, an oligomer combination as above includes a set of first and second amplification oligomers comprising a set of first (A) and second (B) target-hybridizing sequences, respectively, where the set of target-hybridizing sequences is selected from sets (i)-(x) as follows:
(i) (A) SEQ ID NO:48, including RNA equivalents and DNA/RNA chimerics thereof, and
(B) SEQ ID NO:29, 31, 33, 34, 35, 61, 62, 64, 65, or 66, or an RNA equivalent or DNA/RNA chimeric thereof;
(ii) (A) SEQ ID NO:49, including RNA equivalents and DNA/RNA chimerics thereof, and
(B) SEQ ID NO:29, 31, 33, 34, 35, 61, 62, 64, 65, or 66, or an RNA equivalent or DNA/RNA chimeric thereof;
(iii) (A) SEQ ID NO:50, or an RNA equivalent or DNA/RNA chimeric thereof, and
(B) SEQ ID NO:29, 31, 33, 34, 35, 61, 62, 64, 65, or 66, or an RNA equivalent or DNA/RNA chimeric thereof;
(iv) (A) SEQ ID NO:51, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof;
(v) (A) SEQ ID NO:21, or an RNA equivalent or DNA/RNA chimeric thereof, and
(B) SEQ ID NO:29, 30, 31, 33, 34, 35, 54, 61, 62, 64, 65, or 66, or an RNA equivalent or DNA/RNA chimeric thereof;
(vi) (A) SEQ ID NO:22, or an RNA equivalent or DNA/RNA chimeric thereof, and
(B) SEQ ID NO:29, 30, 31, 33, 34, 35, 54, 61, 62, 64, 65, or 66, or an RNA equivalent or DNA/RNA chimeric thereof;
(vii) (A) SEQ ID NO:23, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof;
(viii) (A) SEQ ID NO:24, or an RNA equivalent or DNA/RNA chimeric thereof, and
(B) SEQ ID NO:29, 30, 31, 33, 34, 35, 52, 53, 54, 61, 62, 64, 65, or 66, or an RNA equivalent or DNA/RNA chimeric thereof;
(ix) (A) SEQ ID NO:56, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof; and
(x) (A) SEQ ID NO:45, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof.

In certain embodiments comprising an amplification oligomer having the target-hybridizing sequence of SEQ ID NO:56, the nucleobase at position 1 of SEQ ID NO:56 is guanine (G) SEQ ID NO:46, or an RNA equivalent or DNA/RNA chimeric thereof). In particular variations, the set of target-hybridizing sequences A and B is selected from sets (i)-(ix) as follows:
(i) (A) SEQ ID NO:49, including RNA equivalents and DNA/RNA chimerics thereof, and
(B) SEQ ID NO:29 or 31, or an RNA equivalent or DNA/RNA chimeric thereof;
(ii) (A) SEQ ID NO:50, or an RNA equivalent or DNA/RNA chimeric thereof, and
(B) SEQ ID NO:29 or 31, or an RNA equivalent or DNA/RNA chimeric thereof;
(iii) (A) SEQ ID NO:51, or an RNA equivalent or DNA/RNA chimeric thereof, and
(B) SEQ ID NO:29, 31, 65, or 66, or an RNA equivalent or DNA/RNA chimeric thereof;
(iv) (A) SEQ ID NO:21, or an RNA equivalent or DNA/RNA chimeric thereof, and
(B) SEQ ID NO:29, or an RNA equivalent or DNA/RNA chimeric thereof;
(v) (A) SEQ ID NO:22, or an RNA equivalent or DNA/RNA chimeric thereof, and
(B) SEQ ID NO:31, 61, 62, 64, or 66, or an RNA equivalent or DNA/RNA chimeric thereof;
(vi) (A) SEQ ID NO:23, or an RNA equivalent or DNA/RNA chimeric thereof, and
(B) SEQ ID NO:33, 34, 35, 62, 65, or 66, or an RNA equivalent or DNA/RNA chimeric thereof;
(vii) (A) SEQ ID NO:24, or an RNA equivalent or DNA/RNA chimeric thereof, and
(B) SEQ ID NO:54, 62, or 64, or an RNA equivalent or DNA/RNA chimeric thereof;
(viii) (A) SEQ ID NO:56, or an RNA equivalent or DNA/RNA chimeric thereof, and
(B) SEQ ID NO:29, 30, 33, 34, 35, 61, 62, 64, 65, or 66, or an RNA equivalent or DNA/RNA chimeric thereof; and
(ix) (A) SEQ ID NO:45, or an RNA equivalent or DNA/RNA chimeric thereof, and (B) SEQ ID NO:31, 33, 34, 35, 53, 61, 62, 64, 65, or 66, or an RNA equivalent or DNA/RNA chimeric thereof.

In some embodiments of an oligomer combination as above, an amplification oligomer as in (b) is a promoter primer further including a promoter sequence (e.g., a T7 promoter sequence) located 5' to the target-hybridizing sequence. A particularly suitable promoter sequence is a T7 promoter sequence having the sequence shown in SEQ ID NO:73.

In certain embodiments, an oligomer combination further includes at least one detection probe oligomer. In particular embodiments, the detection probe oligomer includes a target-hybridizing sequence that is from about 14 to about 28 nucleotides in length and is configured to specifically hybridize to a target sequence contained within SEQ ID NO:39 or the complement thereof. In specific variations, the detection probe target-hybridizing sequence is selected from SEQ ID NO:37, SEQ ID NO:55, SEQ ID NO:67, and SEQ ID NO:71, including complements, DNA equivalents, and DNA/RNA chimerics thereof. A detection probe oligomer may contain a 2'-methoxy backbone at one or more linkages in the nucleic acid backbone.

In some variations, an oligomer combination includes at least two detection probe oligomers. For example, an oligomer combination may include at least two detection probe oligomers comprising a target-hybridizing sequence that is from about 14 to about 28 nucleotides in length and is configured to specifically hybridize to a target sequence contained within SEQ ID NO:39 or the complement thereof. In some such embodiments, each detection probe target-hybridizing sequence is individually selected from SEQ ID NO:37, SEQ ID NO:55, SEQ ID NO:67, and SEQ ID NO:71, including complements, DNA equivalents, and DNA/RNA chimerics thereof. In a specific variation, an oligomer combination includes a first detection probe oligomer comprising the target hybridizing sequence of SEQ ID NO:55 or its complement, or an RNA equivalent or DNA/RNA chimeric thereof, and a second detection probe oligomer comprising the target hybridizing sequence of SEQ ID NO:67 or its complement, or an RNA equivalent or DNA/RNA chimeric thereof. In other variations, the oligomer combination includes at least three detection probe oligomers. For example, at least three detection probe oligomers may include a first detection probe oligomer comprising the target hybridizing sequence of SEQ ID NO:37 or its complement, or an RNA equivalent or DNA/RNA chimeric thereof; a second detection probe oligomer comprising the target hybridizing sequence of SEQ ID NO:67 or its complement, or an RNA equivalent or DNA/RNA chimeric thereof; and a third detection probe oligomers comprising the target-hybridizing sequence of SEQ ID NO:71 or its complement, or an RNA equivalent or DNA/RNA chimeric thereof. One or more (e.g., each) of the at least two detection probe oligomers may contain a 2'-methoxy backbone at one or more linkages in the nucleic acid backbone.

In some embodiments, an oligomer combination further includes a capture probe oligomer comprising a target-hybridizing sequence covalently attached to a sequence or moiety that binds to an immobilized probe. Particularly suitable target-hybridizing sequences include the sequences shown in SEQ ID NO:4 and SEQ ID NO:42, including complements, DNA equivalents, and DNA/RNA chimerics thereof. In some variations comprising a target-hybridizing sequence of SEQ ID NO:4, the nucleobase at position 20 of SEQ ID NO:4 is adenine (A). In some such variations, the nucleobase at position 19 of SEQ ID NO:4 is cytosine (C) or uracil (U). In more specific variations, the capture probe oligomer has a sequence selected from SEQ ID NO:3, SEQ ID NO:7, and SEQ ID NO:43. In certain embodiments, an oligomer combination further includes at least two or at least three capture probe oligomers as above. For example, an oligomer combination may include a first capture probe oligomer comprising the target-hybridizing sequence of SEQ ID NO:2 or its complement, or a DNA equivalent or DNA/RNA chimeric thereof; a second capture probe oligomer comprising the target-hybridizing sequence of SEQ ID NO:6 or its complement, or a DNA equivalent or DNA/RNA chimeric thereof; and a third capture probe oligomer comprising the target-hybridizing sequence of SEQ ID NO:42 or its complement, or a DNA equivalent or DNA/RNA chimeric thereof. In a more particular variation, the first, second, and third capture probe oligomers respectively have the sequences of SEQ ID NO:3, SEQ ID NO:7, and SEQ ID NO:43.

In other aspects, the present invention provides a kit or a reaction mixture comprising an oligomer combination as above.

In yet another aspect, the present invention provides a method for determining the presence or absence of hepatitis E virus (HEV) in a sample. The method generally includes the following steps: (1) contacting a sample, suspected of containing HEV, with at least two oligomers for amplifying a target region of an HEV target nucleic acid; (2) performing an in vitro nucleic acid amplification reaction, where any HEV target nucleic acid present in the sample is used as a template for generating an amplification product; and (3) detecting the presence or absence of the amplification product, thereby determining the presence or absence of HEV in the sample. The at least two amplification oligomers include (a) at least one amplification oligomer selected from (i) an oligomer comprising a target-hybridizing sequence that is from about 14 to about 23 contiguous nucleotides contained in the sequence of SEQ ID NO:63 and that includes at least the sequence of SEQ ID NO:26, including RNA equivalents and DNA/RNA chimerics thereof, and (ii) an oligomer comprising a target-hybridizing sequence that is from about 14 to about 23 contiguous nucleotides contained in the sequence of SEQ ID NO:16, including RNA equivalents and DNA/RNA chimerics thereof; and (b) at least one amplification oligomer comprising a target-hybridizing sequence that is from about 17 to about 28 contiguous nucleotides contained in the sequence of SEQ ID NO:47 and that includes at least the sequence of SEQ ID NO:25, including RNA equivalents and DNA/RNA chimerics thereof.

Suitable amplification oligomers as specified above in (a) include oligomers comprising a target-hybridizing sequence selected from SEQ ID NO:29, SEQ ID NO:30, SEQ ID NO:31, SEQ ID NO:32, SEQ ID NO:33, SEQ ID NO:34, SEQ ID NO:35, SEQ ID NO:52, SEQ ID NO:53, SEQ ID NO:54, SEQ ID NO:61, SEQ ID NO:62, SEQ ID NO:64, SEQ ID NO:65, and SEQ ID NO:66, including RNA equivalents and DNA/RNA chimerics thereof. In some preferred variations, an amplification oligomer of (a) comprises a target-hybridizing sequence selected from SEQ ID NO:29, SEQ ID NO:31, SEQ ID NO:32, SEQ ID NO:33, SEQ ID NO:34, SEQ ID NO:35, SEQ ID NO:61, SEQ ID NO:62, SEQ ID NO:64, SEQ ID NO:65, and SEQ ID NO:66, including RNA equivalents and DNA/RNA chimerics thereof. In some embodiments, an amplification oligomer of (a) comprises a target-hybridizing sequence that is from about 14 to about 20 nucleotides contained in the sequence of SEQ ID NO:13 (e.g., SEQ ID NO:33, SEQ ID NO:34, SEQ ID NO:35, SEQ ID NO:62, SEQ ID NO:64, SEQ ID NO:65, or SEQ ID NO:66).

In certain variations a method for determining the presence or absence of HEV, an amplification oligomer as specified in (a) comprises a target-hybridizing sequence that is from 15 to 17 nucleotides contained in the sequence of SEQ ID NO:16 and that includes at least the sequence of SEQ ID NO:27, including RNA equivalents and DNA/RNA chimerics thereof (e.g., a target-hybridizing sequence selected from SEQ ID NO:29, SEQ ID NO:30, SEQ ID NO:31, and SEQ ID NO:32, including RNA equivalents and DNA/RNA chimerics thereof). In some embodiments, an amplification oligomer of (a) comprises a target-hybridizing sequence of SEQ ID NO:28, including RNA equivalents and DNA/RNA chimerics thereof (e.g., a target-hybridizing sequence selected from SEQ ID NO:29 and SEQ ID NO:32, including RNA equivalents and DNA/RNA chimerics thereof).

Suitable amplification oligomers as specified above in (b) include oligomers comprising a target-hybridizing sequence selected from SEQ ID NO:21, SEQ ID NO:22, SEQ ID NO:23, SEQ ID NO:24, SEQ ID NO:45, SEQ ID NO:46, SEQ ID NO:48, SEQ ID NO:49, SEQ ID NO:50, SEQ ID NO:51, and SEQ ID NO:56, including RNA equivalents and DNA/RNA chimerics thereof. In some preferred variations, an amplification oligomer of (b) comprises a target-hybridizing sequence selected from SEQ ID NO:24 and SEQ ID NO:56, including RNA equivalents and DNA/RNA chimerics thereof. In other preferred variations, an amplification oligomer of (b) comprises a target-hybridizing sequence selected from SEQ ID NO:22, SEQ ID NO:23, SEQ ID NO:45, SEQ ID NO:46, and SEQ ID NO:51, including RNA equivalents and DNA/RNA chimerics thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

In some embodiments of a method as above for determining the presence or absence HEV, the least two amplification oligomers include an amplification oligomer as specified in (a)(i) and an amplification oligomer as specified in (a)(ii). In some such embodiments, the amplification oligomer of (a)(i) comprises a target-hybridizing sequence selected from SEQ ID NO:33, SEQ ID NO:34, SEQ ID NO:35, SEQ ID NO:61, SEQ ID NO:62, SEQ ID NO:64, SEQ ID NO:65, and SEQ ID NO:66, including RNA equivalents and DNA/RNA chimerics thereof. In certain preferred variations, the amplification oligomer of (a)(i) comprises a target-hybridizing sequence selected from SEQ ID NO:62, SEQ ID NO:64, SEQ ID NO:65, and SEQ ID NO:66, including RNA equivalents and DNA/RNA chimerics thereof.

In certain embodiments of the method in which an amplification oligomer as specified in (a)(i) and an amplification oligomer as specified in (a)(ii) are used for amplification of the HEV target region, the amplification oligomer of (a)(ii) comprises a target-hybridizing sequence selected from SEQ ID NO:29, SEQ ID NO:30, SEQ ID NO:31, SEQ ID NO:32, SEQ ID NO:52, SEQ ID NO:53, and SEQ ID NO:54, including RNA equivalents and DNA/RNA chimerics thereof. In certain preferred variations, the amplification oligomer of (a)(ii) comprises a target-hybridizing sequence selected from SEQ ID NO:29, SEQ ID NO:31, and SEQ ID NO:32, including RNA equivalents and DNA/RNA chimerics thereof. In particular variations, (I) the amplification oligomer of (a)(i) comprises the target-hybridizing sequence of SEQ ID NO:64, or an RNA equivalent or DNA/RNA chimeric thereof, and the amplification oligomer of (a)(ii) comprises the target-hybridizing sequence of SEQ ID NO:29, or an RNA equivalent or DNA/RNA chimeric thereof; or (II) the amplification oligomer of (a)(i) comprises the target-hybridizing sequence of SEQ ID NO:65, or an RNA equivalent or DNA/RNA chimeric thereof, and the amplification oligomer of (a)(ii) comprises the target-hybridizing sequence of SEQ ID NO:29 or SEQ ID NO:31, or an RNA equivalent or DNA/RNA chimeric thereof.

In some embodiments of a method as above for determining the presence or absence HEV, a combination of at least two oligomers as above includes a first amplification oligomer as specified in (a)(ii) and a second amplification oligomer as specified in (a)(ii). In some such embodiments, each of the first and second amplification oligomer as in (a)(ii) comprises a target-hybridizing sequence that is from 15 to 17 nucleotides contained in the sequence of SEQ ID NO:16 and that includes at least the sequence of SEQ ID NO:27, including RNA equivalents and DNA/RNA chimerics thereof (e.g., a target-hybridizing sequence selected from SEQ ID NO:29, SEQ ID NO:30, SEQ ID NO:31, and SEQ ID NO:32, including RNA equivalents and DNA/RNA chimerics thereof). In certain variations, each of the first and second amplification oligomers of (a)(ii) comprises a target-hybridizing sequence of SEQ ID NO:28, including RNA equivalents and DNA/RNA chimerics thereof. In a particular variations, the first amplification oligomer of (a)(ii) comprises the target hybridizing sequence of SEQ ID NO:29, or an RNA equivalent or DNA/RNA chimeric thereof, and the second amplification oligomer of (a)(ii) comprises the target hybridizing sequence of SEQ ID NO:32, or an RNA equivalent or DNA/RNA chimeric thereof.

In some embodiments of a method as above, the amplifying step utilizes first and second amplification oligomers as specified in (b). In some such embodiments, the first amplification oligomer of (b) comprises a target-hybridizing sequence selected from SEQ ID NO:24 and SEQ ID NO:56, including RNA equivalents and DNA/RNA chimerics thereof. In other embodiments, the first amplification oligomer of (b) comprises a target-hybridizing sequence selected from SEQ ID NO:22, SEQ ID NO:23, SEQ ID NO:45, SEQ ID NO:46, and SEQ ID NO:51, including RNA equivalents and DNA/RNA chimerics thereof. In particular variations, (I) the first amplification oligomer of (b) comprises the target-hybridizing sequence of SEQ ID NO:24, or an RNA equivalent or DNA/RNA chimeric thereof, and the second amplification oligomer of (b) comprises the target-hybridizing sequence of SEQ ID NO:56, or an RNA equivalent or DNA/RNA chimeric thereof; or (II) the first amplification oligomer of (b) comprises the target-hybridizing sequence of SEQ ID NO:23 or SEQ ID NO:51, or an RNA equivalent or DNA/RNA chimeric thereof, and the second amplification oligomer of (b) comprises the target-hybridizing sequence of SEQ ID NO:45, or an RNA equivalent or DNA/RNA chimeric thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

For amplifying the HEV target region in a method as above, an amplification oligomer as in (a)(i), an amplification oligomer as in (a)(ii), a first amplification oligomer as in (b), and a second amplification oligomer as in (b) may be used. In a particular variation, the amplification oligomer of (a)(i) comprises the target-hybridizing sequence of SEQ ID NO:64, or an RNA equivalent or DNA/RNA chimeric thereof; the amplification oligomer of (a)(ii) comprises the target-hybridizing sequence of SEQ ID NO:29, or an RNA equivalent or DNA/RNA chimeric thereof; the first amplification oligomer of (b) comprises the target-hybridizing sequence of SEQ ID NO:24, or an RNA equivalent or DNA/RNA chimeric thereof; and the second amplification oligomer of (b) comprises the target-hybridizing sequence of SEQ ID NO:56, or an RNA equivalent or DNA/RNA chimeric thereof. In another variation, the amplification oligomer of (a)(i) comprises the target-hybridizing sequence of SEQ ID NO:29, or an RNA equivalent or DNA/RNA chimeric thereof; the amplification oligomer of (a)(ii) comprises the target-hybridizing sequence of SEQ ID NO:65; or an RNA equivalent or DNA/RNA chimeric thereof, the first amplification oligomer of (b) comprises the target-hybridizing sequence of SEQ ID NO:24; or an RNA equivalent or DNA/RNA chimeric thereof; and the second amplification oligomer of (b) comprises the target-hybridizing sequence of SEQ ID NO:56, or an RNA equivalent or DNA/RNA chimeric thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

In other embodiments for amplifying the HEV target region in a method as above, a first amplification oligomer as in (a)(ii), a second amplification oligomer as in (a)(ii), a first amplification oligomer as in (b), and a second amplification oligomer as in (b) may be used. In a particular variation, the first amplification oligomer of (a)(ii) comprises the target-hybridizing sequence of SEQ ID NO:29, or an RNA equivalent or DNA/RNA chimeric thereof; the second amplification oligomer of (a)(ii) comprises the target-hybridizing sequence of SEQ ID NO:32, or an RNA equivalent or DNA/RNA chimeric thereof; the first amplification oligomer of (b) comprises the target-hybridizing sequence of SEQ ID NO:24, or an RNA equivalent or DNA/RNA chimeric thereof; and the second amplification oligomer of (b) comprises the target-hybridizing sequence of SEQ ID NO:46, or an RNA equivalent or DNA/RNA chimeric thereof.

In yet other embodiments of a method for determining the presence or absence of HEV as above, an amplification oligomer of (a) comprises a target-hybridizing sequence selected from SEQ ID NO:29, SEQ ID NO:62, SEQ ID NO:64, SEQ ID NO:65, and SEQ ID NO:66, including RNA equivalents and DNA/RNA chimerics thereof, and an amplification oligomer of (b) comprises a target-hybridizing sequence selected from SEQ ID NO:24 and SEQ ID NO:56, including RNA equivalents and DNA/RNA chimerics thereof. In some such embodiments, the amplifying step uses an oligomer combination that includes a set of first, second, and third amplification oligomers comprising a set of first, second, and third target-hybridizing sequences, respectively, where the set of target-hybridizing sequences is selected from sets (i)-(vi) as follows: (i) SEQ ID NO:65, SEQ ID NO:29, and SEQ ID NO:24, including RNA equivalents and DNA/RNA chimerics thereof; (ii) SEQ ID NO:65, SEQ ID NO:29, and SEQ ID NO:56, including RNA equivalents and DNA/RNA chimerics thereof; (iii) SEQ ID NO:29, SEQ ID NO:24, and SEQ ID NO:56, including RNA equivalents and DNA/RNA chimerics thereof; (iv) SEQ ID NO:66, SEQ ID NO:24, and SEQ ID NO:56, including RNA equivalents and DNA/RNA chimerics thereof; (v) SEQ ID NO:65, SEQ ID NO:24, and SEQ ID NO:56, including RNA equivalents and DNA/RNA chimerics thereof; and (vi) SEQ ID NO:62, SEQ ID NO:29, and SEQ ID NO:56, including RNA equivalents and DNA/RNA chimerics thereof. In certain variations comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof).

In some embodiments, the amplifying step uses an oligomer combination that includes a set of first and second amplification oligomers comprising a set of first (A) and second (B) target-hybridizing sequences, respectively, where the set of target-hybridizing sequences is selected from sets (i)-(xiv) as follows:

(i) (A) SEQ ID NO:54, including RNA equivalents and DNA/RNA chimerics thereof, and
  (B) SEQ ID NO:21, 22, 23, 24, 45, 56, or 51, or an RNA equivalent or DNA/RNA chimeric thereof;
(ii) (A) SEQ ID NO:53, including RNA equivalents and DNA/RNA chimerics thereof, and
  (B) SEQ ID NO:23, 24, 45, 56, or 51, or an RNA equivalent or DNA/RNA chimeric thereof;
(iii) (A) SEQ ID NO:52, or an RNA equivalent or DNA/RNA chimeric thereof, and
  (B) SEQ ID NO:24, or an RNA equivalent or DNA/RNA chimeric thereof;
(iv) (A) SEQ ID NO:31, or an RNA equivalent or DNA/RNA chimeric thereof, and
  (B) SEQ ID NOs:21, 22, 23, 24, 45, 56, 48, 49, 50, or 51, or an RNA equivalent or DNA/RNA chimeric thereof;
(v) (A) SEQ ID NO:30, or an RNA equivalent or DNA/RNA chimeric thereof, and
  (B) SEQ ID NO:21, 22, 23, 24, 45, 56, 50, or 51, or an RNA equivalent or DNA/RNA chimeric thereof;
(vi) (A) SEQ ID NO:29, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(vii) (A) SEQ ID NO:66, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(viii) (A) SEQ ID NO:65, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(ix) (A) SEQ ID NO:64, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(x) (A) SEQ ID NO:62, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(xi) (A) SEQ ID NO:35, or an RNA equivalent or DNA/RNA chimeric thereof, and
  (B) SEQ ID NO:21, 22, 23, 24, 45, 56, 48, 49, 50, or 51, or an RNA equivalent or DNA/RNA chimeric thereof;
(xii) (A) SEQ ID NO:34, or an RNA equivalent or DNA/RNA chimeric thereof, and (B) SEQ ID NO:21, 22, 23, 24, 45, 56, 48, 49, 50, or 51, or an RNA equivalent or DNA/RNA chimeric thereof;
(xiii) (A) SEQ ID NO:33, or an RNA equivalent or DNA/RNA chimeric thereof, and
(B) SEQ ID NO:21, 22, 23, 24, 45, 56, 48, 49, 50, or 51, or an RNA equivalent or DNA/RNA chimeric thereof; and
(xiv) (A) SEQ ID NO:61, or an RNA equivalent or DNA/RNA chimeric thereof, and
(B) SEQ ID NO:21, 22, 23, 24, 45, 56, 48, 49, 50, or 51, or an RNA equivalent or DNA/RNA chimeric thereof.

In certain embodiments comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof). In particular variations, the set of target-hybridizing sequences A and B is selected from sets (i)-(xiii) as follows:
(i) (A) SEQ ID NO:54, or an RNA equivalent or DNA/RNA chimeric thereof, and
(B) SEQ ID NO:24, or an RNA equivalent or DNA/RNA chimeric thereof;
(ii) (A) SEQ ID NO:53, or an RNA equivalent or DNA/RNA chimeric thereof, and
(B) SEQ ID NO:45, or an RNA equivalent or DNA/RNA chimeric thereof;
(iii) (A) SEQ ID NO:31, or an RNA equivalent or DNA/RNA chimeric thereof, and
(B) SEQ ID NO:22, 45, 49, 50, or 51, or an RNA equivalent or DNA/RNA chimeric thereof;
(iv) (A) SEQ ID NO:30, or an RNA equivalent or DNA/RNA chimeric thereof, and
(B) SEQ ID NO:56, or an RNA equivalent or DNA/RNA chimeric thereof;
(v) (A) SEQ ID NO:29, or an RNA equivalent or DNA/RNA chimeric thereof, and
(B) SEQ ID NO:21, 56, 48, 50, or 51, or an RNA equivalent or DNA/RNA chimeric thereof;
(vi) (A) SEQ ID NO:66, or an RNA equivalent or DNA/RNA chimeric thereof, and
(B) SEQ ID NO:22, 23, 45, 56, or 51, or an RNA equivalent or DNA/RNA chimeric thereof;
(vii) (A) SEQ ID NO:65, or an RNA equivalent or DNA/RNA chimeric thereof, and
(B) SEQ ID NO:23, 45, 56, or 51, or an RNA equivalent or DNA/RNA chimeric thereof;
(viii) (A) SEQ ID NO:64, or an RNA equivalent or DNA/RNA chimeric thereof, and
(B) SEQ ID NO:22, 24, 45, 56, or 50, or an RNA equivalent or DNA/RNA chimeric thereof;
(ix) (A) SEQ ID NO:62, or an RNA equivalent or DNA/RNA chimeric thereof, and
(B) SEQ ID NO:22, 23, 24, 45, or 56, or an RNA equivalent or DNA/RNA chimeric thereof;
(x) (A) SEQ ID NO:35, or an RNA equivalent or DNA/RNA chimeric thereof, and
(B) SEQ ID NO:23, 45, or 56, or an RNA equivalent or DNA/RNA chimeric thereof;
(xi) (A) SEQ ID NO:34, or an RNA equivalent or DNA/RNA chimeric thereof, and
(B) SEQ ID NO:23, 45, or 56, or an RNA equivalent or DNA/RNA chimeric thereof;
(xii) (A) SEQ ID NO:33, or an RNA equivalent or DNA/RNA chimeric thereof, and
(B) SEQ ID NO:23, 45, or 56, or an RNA equivalent or DNA/RNA chimeric thereof; and
(xiii) (A) SEQ ID NO:61, or an RNA equivalent or DNA/RNA chimeric thereof, and
(B) SEQ ID NO:22, 45, or 56, or an RNA equivalent or DNA/RNA chimeric thereof.

In still other embodiments, the amplifying step uses an oligomer combination that includes a set of first and second amplification oligomers comprising a set of first (A) and second (B) target-hybridizing sequences, respectively, where the set of target-hybridizing sequences is selected from sets (i)-(x) as follows:
(i) (A) SEQ ID NO:48, including RNA equivalents and DNA/RNA chimerics thereof, and
(B) SEQ ID NO:29, 31, 33, 34, 35, 61, 62, 64, 65, or 66, or an RNA equivalent or DNA/RNA chimeric thereof;
(ii) (A) SEQ ID NO:49, including RNA equivalents and DNA/RNA chimerics thereof, and
(B) SEQ ID NO:29, 31, 33, 34, 35, 61, 62, 64, 65, or 66, or an RNA equivalent or DNA/RNA chimeric thereof;
(iii) (A) SEQ ID NO:50, or an RNA equivalent or DNA/RNA chimeric thereof, and
(B) SEQ ID NO:29, 31, 33, 34, 35, 61, 62, 64, 65, or 66, or an RNA equivalent or DNA/RNA chimeric thereof;
(iv) (A) SEQ ID NO:51, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof;
(v) (A) SEQ ID NO:21, or an RNA equivalent or DNA/RNA chimeric thereof, and
(B) SEQ ID NO:29, 30, 31, 33, 34, 35, 54, 61, 62, 64, 65, or 66, or an RNA equivalent or DNA/RNA chimeric thereof;
(vi) (A) SEQ ID NO:22, or an RNA equivalent or DNA/RNA chimeric thereof, and
(B) SEQ ID NO:29, 30, 31, 33, 34, 35, 54, 61, 62, 64, 65, or 66, or an RNA equivalent or DNA/RNA chimeric thereof;
(vii) (A) SEQ ID NO:23, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof;
(viii) (A) SEQ ID NO:24, or an RNA equivalent or DNA/RNA chimeric thereof, and
(B) SEQ ID NO:29, 30, 31, 33, 34, 35, 52, 53, 54, 61, 62, 64, 65, or 66, or an RNA equivalent or DNA/RNA chimeric thereof;
(ix) (A) SEQ ID NO:56, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof; and
(x) (A) SEQ ID NO:45, or an RNA equivalent or DNA/RNA chimeric thereof, and
(B) SEQ ID NO:29, 30, 31, 33, 34, 35, 53, 54, 61, 62, 64, 65, or 66, or an RNA equivalent or DNA/RNA chimeric thereof.

In certain embodiments comprising an amplification oligomer having the target-hybridizing sequence of SEQ ID NO:56, the nucleobase at position 1 of SEQ ID NO:56 is guanine (G) (i.e., SEQ ID NO:46, or an RNA equivalent or DNA/RNA chimeric thereof). In particular variations, the set of target-hybridizing sequences A and B is selected from sets (i)-(ix) as follows:
- (i) (A) SEQ ID NO:49, including RNA equivalents and DNA/RNA chimerics thereof, and
    - (B) SEQ ID NO:29 or 31, or an RNA equivalent or DNA/RNA chimeric thereof;
- (ii) (A) SEQ ID NO:50, or an RNA equivalent or DNA/RNA chimeric thereof, and
    - (B) SEQ ID NO:29 or 31, or an RNA equivalent or DNA/RNA chimeric thereof;
- (iii) (A) SEQ ID NO:51, or an RNA equivalent or DNA/RNA chimeric thereof, and
    - (B) SEQ ID NO:29, 31, 65, or 66, or an RNA equivalent or DNA/RNA chimeric thereof;
- (iv) (A) SEQ ID NO:21, or an RNA equivalent or DNA/RNA chimeric thereof, and
    - (B) SEQ ID NO:29, or an RNA equivalent or DNA/RNA chimeric thereof;
- (v) (A) SEQ ID NO:22, or an RNA equivalent or DNA/RNA chimeric thereof, and
    - (B) SEQ ID NO:31, 61, 62, 64, or 66, or an RNA equivalent or DNA/RNA chimeric thereof;
- (vi) (A) SEQ ID NO:23, or an RNA equivalent or DNA/RNA chimeric thereof, and
    - (B) SEQ ID NO:33, 34, 35, 62, 65, or 66, or an RNA equivalent or DNA/RNA chimeric thereof;
- (vii) (A) SEQ ID NO:24, or an RNA equivalent or DNA/RNA chimeric thereof, and
    - (B) SEQ ID NO:54, 62, or 64, or an RNA equivalent or DNA/RNA chimeric thereof;
- (viii) (A) SEQ ID NO:56, or an RNA equivalent or DNA/RNA chimeric thereof, and
    - (B) SEQ ID NO:29, 30, 33, 34, 35, 61, 62, 64, 65, or 66, or an RNA equivalent or DNA/RNA chimeric thereof; and
- (ix) (A) SEQ ID NO:45, or an RNA equivalent or DNA/RNA chimeric thereof, and
    - (B) SEQ ID NO:31, 33, 34, 35, 53, 61, 62, 64, 65, or 66, or an RNA equivalent or DNA/RNA chimeric thereof.

In some embodiments of a method for determining the presence or absence of HEV as above, an amplification oligomer as in (b) is a promoter primer further including a promoter sequence (e.g., a T7 promoter sequence) located 5' to the target-hybridizing sequence. A particularly suitable promoter sequence is a T7 promoter sequence having the sequence shown in SEQ ID NO:73.

Typically, the method for determining the presence or absence of HEV further includes purifying the HEV target nucleic acid from other components in the sample before the amplification step (1). In particular embodiments, the purifying step includes contacting the sample with at least one capture probe oligomer comprising a target-hybridizing sequence covalently attached to a sequence or moiety that binds to an immobilized probe. Particularly suitable target-hybridizing sequences include the sequences shown in SEQ ID NO:4 and SEQ ID NO:42, including complements, DNA equivalents, and DNA/RNA chimerics thereof. In some variations of the method comprising the use of a target-hybridizing sequence of SEQ ID NO:4, the nucleobase at position 20 of SEQ ID NO:4 is adenine (A). In some such variations, the nucleobase at position 19 of SEQ ID NO:4 is cytosine (C) or uracil (U). In more specific variations, the capture probe oligomer has a sequence selected from SEQ ID NO:3, SEQ ID NO:7, and SEQ ID NO:43. In certain embodiments, the purifying step includes the use of at least two or at least three capture probe oligomers as above. For example, the purifying step may include using a first capture probe oligomer comprising the target-hybridizing sequence of SEQ ID NO:2 or its complement, or a DNA equivalent or DNA/RNA chimeric thereof; a second capture probe oligomer comprising the target-hybridizing sequence of SEQ ID NO:6 or its complement, or a DNA equivalent or DNA/RNA chimeric thereof; and a third capture probe oligomer comprising the target-hybridizing sequence of SEQ ID NO:42 or its complement, or a DNA equivalent or DNA/RNA chimeric thereof. In a more particular variation, the first, second, and third capture probe oligomers respectively have the sequences of SEQ ID NO:3, SEQ ID NO:7, and SEQ ID NO:43.

In some embodiments, the detecting step (3) includes contacting the in vitro nucleic acid amplification reaction with at least one detection probe oligomer configured to specifically hybridize to the amplification product under conditions whereby the presence or absence of the amplification product is determined, thereby determining the presence or absence of HEV in the sample. In particular embodiments, the detection probe oligomer includes a target-hybridizing sequence that is from about 14 to about 28 nucleotides in length and is configured to specifically hybridize to a target sequence contained within SEQ ID NO:39 or the complement thereof. In specific variations, the detection probe target-hybridizing sequence is selected from SEQ ID NO:37, SEQ ID NO:55, SEQ ID NO:67, and SEQ ID NO:71, including complements, DNA equivalents, and DNA/RNA chimerics thereof. A detection probe oligomer may contain a 2'-methoxy backbone at one or more linkages in the nucleic acid backbone.

In some variations, the detecting step includes contacting the in vitro nucleic acid amplification reaction with at least two detection probe oligomers. For example, the in vitro nucleic acid amplification reaction may be contacted with at least two detection probe oligomers comprising a target-hybridizing sequence that is from about 14 to about 28 nucleotides in length and is configured to specifically hybridize to a target sequence contained within SEQ ID NO:39 or the complement thereof. In some such embodiments, each detection probe target-hybridizing sequence is individually selected from SEQ ID NO:37, SEQ ID NO:55, SEQ ID NO:67, and SEQ ID NO:71, including complements, DNA equivalents, and DNA/RNA chimerics thereof. In a specific variation, the detecting step includes contacting the in vitro nucleic acid amplification reaction with a first detection probe oligomer comprising the target hybridizing sequence of SEQ ID NO:55 or its complement, or an RNA equivalent or DNA/RNA chimeric thereof, and a second detection probe oligomer comprising the target hybridizing sequence of SEQ ID NO:67 or its complement, or an RNA equivalent or DNA/RNA chimeric thereof. In other variations, the detecting step includes contacting the in vitro nucleic acid amplification reaction with at least three detection probe oligomers. The at least three detection probe oligomers may include a first detection probe oligomer comprising the target hybridizing sequence of SEQ ID NO:37 or its complement, or an RNA equivalent or DNA/RNA chimeric thereof; a second detection probe oligomer comprising the target hybridizing sequence of SEQ ID NO:67 or its complement, or an RNA equivalent or DNA/RNA chimeric thereof; and a third detection probe oligomers comprising the target-hybridizing sequence of SEQ ID NO:71 or its complement, or an RNA equivalent or DNA/RNA chimeric thereof. One or more (e.g., each) of the at least two detection probe oligomers may contain a 2'-methoxy backbone at one or more linkages in the nucleic acid backbone.

In some embodiments of a method utilizing a detection probe oligomer, the detection probe includes at least one label. In specific variations, the one or more label(s) are selected from a chemiluminescent label, a fluorescent label, a quencher, or any combination thereof. In certain embodiments, the detecting step (3) detects hybridization of the at least one labeled detection probe oligomer to the amplification product in a homogeneous detection system. A particularly suitable label for use in a homogeneous detection system is a chemiluminescent acridinium ester (AE) compound linked between two nucleobases of the at least one detection probe oligomer.

In certain variations of a method for determining the presence or absence of HEV as above, the amplification reaction at step (2) is an isothermal amplification reaction such as, for example, a transcription-mediated amplification (TMA) reaction.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain hepatitis E virus (HEV) (including, e.g., any one of HEV genotypes 1, 2, 3, or 4) or components thereof, such as nucleic acids or fragments of nucleic acids. Samples include "biological samples" which include any tissue or material derived from a living or dead human that may contain HEV or target nucleic acid derived therefrom, including, e.g., peripheral blood, plasma, serum, lymph node, gastrointestinal tissue (e.g., liver), or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Synthetic nucleic acids, e.g., DNA, RNA, DNA/RNA chimerics, (including when non-natural nucleotides or analogues are included therein), are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy"). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to various genotypes of HEV. It is understood that other reasons exist for configuring a target-hybridizing sequence to have less than 100% complementarity to a target nucleic acid.

The term "targets a sequence" as used herein in reference to a region of HEV nucleic acid refers to a process whereby an oligonucleotide hybridizes to the target sequence in a manner that allows for amplification and detection as described herein. In one preferred embodiment, the oligonucleotide is complementary with the targeted HEV nucleic acid sequence and contains no mismatches. In another preferred embodiment, the oligonucleotide is complementary but contains 1, 2, 3, 4, or 5 mismatches with the targeted HEV nucleic acid sequence. Preferably, the oligonucleotide that hybridizes to the HEV nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced HEV target region. Such an oligonucleotide is not limited to targeting that sequence only, but is rather useful as a composition, in a kit, or in a method for targeting a HEV target nucleic acid. The oligonucleotide is designed to function as a component of an assay for amplification and detection of HEV from a sample, and therefore is designed to target HEV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

The term "fragment," as used herein in reference to the HEV targeted nucleic acid, refers to a piece of contiguous nucleic acid. In certain embodiments, the fragment includes contiguous nucleotides from an HEV RNA corresponding to SEQ ID NO:1, wherein the number of contiguous nucleotides in the fragment are less than that for the entire sequence corresponding to SEQ ID NO:1.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is an HEV RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. Preferably, oligonucleotides are synthesized using, for example, a DNA synthesizer and related chemistry (e.g., ABI 3900, Life Technologies, Foster City, Calif.). A synthesized amplification oligomer can, in one aspect, be an oligonucleotide synthesized using an automated synthesizer and phosphoramidite chemistry. In one aspect, the synthesized oligonucleotide is made using phosphoramidite chemistry and the most 3'-terminal hydroxyl group is covalently bound to a solid support. Solid supports include, but are not limited to controlled pore glass (CPG) and macroporous polystyrene (MPPS). In one aspect, the synthesized oligonucleotide is made using phosphoramidite chemistry and the phosphoramidite building block have protective groups attached to their functional groups. Reactive groups include, but are not limited to, dimethoxytrityl (DMT), t-butyldimethylsilyl) groups (TBDMS), tri-iso-propylsilyloxymethyl) group (TOM), and 2-cyanoethyl groups. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase "or its complement, or an RNA equivalent or DNA/RNA chimeric thereof," with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence. Similarly, the phrase "or its complement, or a DNA equivalent or DNA/RNA chimeric thereof," with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence that hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

A "terminating oligonucleotide" is an oligonucleotide comprising a base sequence that is substantially complementary to a sequence within the target nucleic acid in the vicinity of the 5'-end of the target region, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., *Nucleic Acids Res.* 26:2224-9, 1988, incorporated by reference herein.) Other modifications as described elsewhere herein may be utilized in addition to or in place of 2'-O-Me ribonucleotides. For example, a terminating oligonucleotide may comprise PNA or an LNA. (See, e.g., Petersen et al., *J. Mol. Recognit.* 13:44-53, 2000, incorporated by reference herein.) A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. While a terminating oligonucleotide typically or necessarily includes a 3'-blocking moiety, "3'-blocked" oligonucleotides are not necessarily terminating oligonucleotides.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription-associated amplification methods are embodiments of amplification methods used for detection of HEV target sequences as described herein. Variations of transcription-associated amplification are well-known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double-stranded or single-stranded and can include DNA, RNA, or both. For example, DNA-dependent RNA polymerase transcribes single-stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof (e.g., DNA/RNA chimerics) and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or two different regions of the same single-stranded nucleic acid, have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T, or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately detect or quantitate RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of HEV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

BRIEF DESCRIPTION OF THE DRAWINGS

FIGS. 1A-1D illustrate a reference sequence for a hepatitis E virus (HEV) genome (SEQ ID NO:1 residues 1-1,850 (1A), residues 1,851-3,700 (1B), residues 3,701-5,550 (1C), and residues 5,551-7256 (1D)), complete sequence found at GenBank under accession number AB074918.2 and GI:21218075.

DETAILED DESCRIPTION OF THE INVENTION

The present invention provides compositions, kits, and methods for amplifying and detecting hepatitis C virus (HEV) nucleic acid from a sample. Preferably, the samples are biological samples. The compositions, kits, and methods provide oligonucleotide sequences that recognize target sequences of the HEV genome, including target sequences of HEV genotypes 1, 2, 3, and 4, or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of HEV, or for capture of HEV target nucleic acid.

The methods provide for the sensitive and specific detection of HEV nucleic acids. The methods include performing a nucleic acid amplification of an HEV target region and detecting the amplified product by, for example, specifically hybridizing the amplified product with a nucleic acid detection probe that provides a signal to indicate the presence of HEV in the sample. The amplification step includes contacting the sample with one or more amplification oligomers specific for a target sequence in an HEV target nucleic acid to produce an amplified product if HEV nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517;

6,150,097; 6,849,412; 6,835,542; 6,534,274; and 6,361,945; and US Patent Application Pub. Nos. 20060068417A1 and 20060194240A1; each incorporated by reference herein).

Preferred compositions of the instant invention are configured to specifically hybridize to nucleic acid of all four major HEV genotypes (types 1, 2, 3, and 4) with minimal cross-reactivity to other, non-HEV nucleic acids suspected of being in a sample (e.g., other bloodborne pathogens). In certain variations, compositions of the invention further allow detection of sequences that are provisionally designated as belonging to HEV genotype 6. In some aspects, the compositions of the instant invention are configured to specifically hybridize to HEV nucleic acid with minimal cross-reactivity to one or more of hepatitis C virus (HCV), human immunodeficiency virus 1 (HIV 1), hepatitis B virus (HBV), and West Nile virus. In one aspect, the compositions of the instant invention are part of a multiplex system that further includes components and methods for detecting one of more of these organisms.

In certain aspects of the invention, a combination of at least two oligomers is provided for determining the presence or absence of HEV in a sample. Typically, the oligomer combination includes at least two amplification oligomers for amplifying a target region of an HEV target nucleic acid corresponding to the sequence of SEQ ID NO:1. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to an HEV target sequence corresponding to a sequence contained within SEQ ID NO:1 and where the target-hybridizing sequences are selected such that the HEV sequence targeted by antisense THS is situated downstream of the HEV sequence targeted by the sense THS (i.e., the at least two amplification oligomers are situated such that they flank the target region to be amplified). In some variations, an oligomer combination includes (a)(i) an oligomer comprising a target-hybridizing sequence that is from about 14 to about 23 contiguous nucleotides and substantially corresponding to, or identical to, a sequence that is contained in the sequence of SEQ ID NO:63 and that includes at least the sequence of SEQ ID NO:26, or the complement thereof or an RNA equivalent or DNA/RNA chimeric thereof. In some variations, at least one amplification oligomer is (a)(ii) an oligomer comprising a target-hybridizing sequence that is from about 14 to about 23 contiguous nucleotides and substantially corresponding to, or identical to, a sequence that is contained in the sequence of SEQ ID NO:16, or the complement thereof or an RNA equivalent or DNA/RNA chimeric thereof. In some variations, at least one amplification oligomer is (b) an oligomer comprising a target-hybridizing sequence that is from about 17 to about 28 contiguous nucleotides and substantially corresponding to, or identical to, a sequence that is contained in the sequence of SEQ ID NO:47 and that includes at least the sequence of SEQ ID NO:25, or the complement thereof or an RNA equivalent or DNA/RNA chimeric thereof. In more specific embodiments, the at least one amplification oligomer for detecting HEV includes providing the at least one amplification oligomer in an amplification reaction mixture. In one aspect, each of the at least one amplification oligomers is provided in the amplification reaction mixture at a concentration from about 4 pmoles/reaction to about 12 pmoles/reaction (inclusive of all whole and partial numbers of the range (e.g., 4, 4.5, 5, 6.75, 8, 10, 10.25, 11, 12.01)). In some variations, the at least one amplification oligomer is a plurality of amplification oligomers, each of which are provided in the amplification reaction mixture at equal concentrations. In some variations, the at least one amplification oligomer is a plurality of amplification oligomers, each of which are not necessarily provided in the amplification reaction mixture at equal concentrations (e.g., one amplification oligomer is provided at twice the concentration of another amplification oligomer in an amplification reaction mixture).

In variations comprising an amplification oligomer as in (a)(i), (a)(ii), or (b) above, the oligomer combination includes at least one an amplification oligomer comprising an HEV-specific target-hybridizing sequence of the opposite polarity (sense vs. antisense or vice versa) as the target-hybridizing sequence of the oligomer of (a)(i), (a)(ii), or (b), such that at least two amplification oligomers flank a target region to be amplified. In some such embodiments, an oligomer combination includes at least one oligomer as in (a)(i) and/or (a)(ii), and at least one oligomer as in (b), such that the oligomer(s) of (a)(i) and/or (a)(ii) and the oligomer(s) of (b) flank the target region to be amplified. In some such variations, the oligomer combination includes at least one amplification oligomer as in (a)(i), at least one amplification oligomer as in (a)(ii), and at least one amplification oligomer (e.g., two amplification oligomers) as in (b). In other such variations, the oligomer combination includes at least two amplification oligomers as in (b) and at least one amplification oligomer as in either of (a)(i) or (a)(ii).

In more specific embodiments of the present invention, an oligomer combination for determining the presence or absence of HEV in a sample includes (1) at least one amplification oligomer comprising an HEV target-hybridizing region substantially corresponding to at least one sense oligomer sequence depicted in Table 1 below, and (2) at least one amplification oligomer comprising an HEV target hybridizing region substantially corresponding to at least one antisense oligomer sequence depicted in Table 1. In some such embodiments, the oligomer combination includes at least two amplification oligomers of (1) above and/or at least two amplification oligomers of (2) above. In particular variations, the sense and/or antisense target-hybridizing sequence(s) of an amplification oligomer combination comprises or consists of the sense and/or antisense sequence(s) selected from Table 1.

TABLE 1

Exemplary Sense and Antisense Amplification Oligomer Target-hybridizing Sequences for Amplification of HEV Target Regions

| SEQ ID NO: | Sequence | Sense/Antisense[1] |
|---|---|---|
| 21 | AGGGGTTGGTTGGATGAATATAG | Antisense |
| 22 | AGGGGTTGGTTGGATGAATATAGG | Antisense |
| 23 | AGGGGTTGGTTGGATGAATATAGGG | Antisense |
| 24 | AGGGGTTGGTTGGATGAATATAGGGGA | Antisense |
| 28[2] | NCGGCGGTGGTTTCTNN | Sense |
| 29 | CCGGCGGTGGTTTCT | Sense |
| 30 | CCGGCGGTGGTTTCTG | Sense |

TABLE 1-continued

Exemplary Sense and Antisense Amplification Oligomer Target-hybridizing Sequences for Amplification of HEV Target Regions

| SEQ ID NO: | Sequence | Sense/ Antisense[1] |
|---|---|---|
| 31 | CCGGCGGTGGTTTCTGG | Sense |
| 32 | CGGCGGTGGTTTCTGG | Sense |
| 33 | CTATGCTGCCCGCGCC | Sense |
| 34 | CTATGCTGCCCGCGCCA | Sense |
| 35 | CTATGCTGCCCGCGCCAC | Sense |
| 45 | GGCGAAGGGGTTGGTTGGATGAA | Antisense |
| 46 | GGGCGAAGGGGTTGGTTGGATGAA | Antisense |
| 47 | GGTTGGTTGGATGAATATAG | Antisense |
| 49 | GGTTGGTTGGATGAATATAGG | Antisense |
| 50 | GGTTGGTTGGATGAATATAGGG | Antisense |
| 51 | GGTTGGTTGGATGAATATAGGGGA | Antisense |
| 52 | GGTTTCTGGGGTGAC | Sense |
| 53 | GTGGTTTCTGGGGTGA | Sense |
| 54 | GTGGTTTCTGGGGTGAC | Sense |
| 56 | SGGCGAAGGGGTTGGTTGGATGAA | Antisense |
| 61 | TGCCTATGCTGCCCGCGCCAC | Sense |
| 62 | TGCTGCCCGCGCCA | Sense |
| 64 | TGCTGCCCGCGCCAC | Sense |
| 65 | TGCTGCCCGCGCCACC | Sense |
| 66 | TGCTGCCCGCGCCACCG | Sense |

[1]The Sense/Antisense designation of these sequences is for exemplary purposes only. Such designation does not necessarily limit a sequence to the accompanying designation.
[2]N at position 1 is C or is absent, N at position 16 is G or is absent, and N at position 17 is G or is absent. In some embodiments, if N at position 16 is G and N at position 17 is absent, then N at position 1 is C.

In certain embodiments, an amplification oligomer as described herein is a promoter primer or promoter provider further comprising a promoter sequence located 5' to the target-hybridizing sequence and which is non-complementary to the HEV target nucleic acid. For example, in some embodiments of an oligomer combination as described herein for amplification of an HEV target region, an amplification oligomer as described above in (b) (e.g., an amplification oligomer comprising or consisting of an antisense target-hybridizing sequence as shown in Table 1) is a promoter primer further comprising a 5' promoter sequence. In particular embodiments, the promoter sequence is a T7 RNA polymerase promoter sequence such as, for example, a T7 promoter sequence having the sequence shown in SEQ ID NO:73. In specific variations, the amplification oligomer of (b) is a promoter primer having the sequence shown in SEQ ID NO:9, SEQ ID NO:10, SEQ ID NO:11, SEQ ID NO:12, SEQ ID NO:14, SEQ ID NO:15, SEQ ID NO:17, SEQ ID NO:18, SEQ ID NO:18, or SEQ ID NO:20.

In some embodiments, an oligomer combination as described herein further includes a terminating oligonucleotide (also referred to herein as a "blocker" oligonucleotide) comprising comprises a base sequence substantially complementary (e.g., fully complementary) to a sequence contained within the target nucleic acid in the vicinity of the 5'-end of the target region. A terminating oligomer is typically used in combination with, e.g., a promoter provider amplification oligomer, such as, for example, in certain embodiments described herein relating to transcription-mediated amplification (TMA).

In some embodiments, an oligomer combination as described herein further comprises at least one capture probe oligomer comprising a target-hybridizing sequence substantially corresponding to a sequence contained in the complement of SEQ ID NO:1, wherein the target-hybridizing sequence is covalently attached to a sequence or moiety that binds to an immobilized probe. In specific variations, the target-hybridizing sequence comprises or consists of a sequence substantially corresponding to, or identical to, a sequence selected from SEQ ID NO:2, SEQ ID NO:4, SEQ ID NO:6, SEQ ID NO:42, including complements, DNA equivalents, and DNA/RNA chimerics thereof. In more specific variations, the capture probe oligomer has a sequence selected from SEQ ID NO:3, SEQ ID NO:7, and SEQ ID NO:43. An oligomer combination may include at least two (e.g., three) capture probe oligomers as above. In more specific embodiments, the at least one capture probe oligomer includes providing the at least one capture probe oligomer in a target capture reaction mixture. In one aspect, each of the at least one capture probe oligomers is provided in the target capture reaction mixture at a concentration from about 3 pmoles/reaction to about 6 pmoles/reaction (inclusive of all whole and partial numbers of the range (e.g., 4, 4.75, 5.12, 5.98, 6)). When a plurality of at least one capture probe oligomer is used in a target capture reaction the concentration of each capture probe oligomer may be equal to the concentration of the others or there may be varied concentrations, as described herein.

In certain variations, an oligomer combination as described herein further comprises at least one detection probe oligomer configured to specifically hybridize to an HEV target sequence that is amplifiable using the first and second amplification oligomers (e.g., an HEV target sequence that is flanked by the target-hybridizing sequences of the first and second amplification oligomers). In particular embodiments, the detection probe oligomer includes a target-hybridizing sequence that is from about 14 to about 28 nucleotides in length and is configured to specifically hybridize to a target sequence contained within SEQ ID NO:39 or the complement thereof. Particularly suitable detection probe oligomers include, for example, oligomers comprising a target-hybridizing sequence substantially corresponding to, or identical to, a sequence selected from SEQ ID NO:37, SEQ ID NO:55, SEQ ID NO:67, and SEQ ID NO:71, including complements, DNA equivalents, and DNA/RNA chimerics thereof. A detection probe oligomer may contain a 2'-methoxy backbone at one or more linkages in the nucleic acid backbone. In some variations, an oligomer combination includes at least two detection probe oligomers. In more specific embodiments, the at least one detection probe oligomer includes providing the at least one detection probe oligomer in an amplicon detection reaction mixture. In one aspect, each of the at least one detection probe oligomers is provided in the detection reaction mixture at about 2.0 E+06 RLU/reaction to about 6.0 E+06 RLU/reaction (inclusive of all whole and partial numbers of the range (e.g., 2.0 E+06, 2.138 E+06, 3.385 E+06 RLU)). When a plurality of at least one detection probe oligomer is used in a detection reaction the concentration of each detection oligomer may be equal to the concentration of the others or there may be varied concentrations, as described herein.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. No. 5,118,801 and U.S. Pat. No. 5,312,728, supra). Methods for using such hairpin probes are well-known in the art.

In yet other embodiments, a detection probe is a linear oligomers that does not substantially form conformations held by intramolecular bonds. In specific variations, a linear detection probe oligomer includes a chemiluminescent compound as the label, preferably an acridinium ester (AE) compound.

In yet other variations, an oligomer combination for detection of an HEV nucleic acid further comprises a probe protection oligomer substantially complementary to a detection probe oligomer. A probe protection oligomer may be hybridized to a substantially complementary, labeled detection probe oligomer (e.g., a probe labeled with a chemiluminescent compound) to stabilize the labeled probe during storage. In specific embodiments, a probe protection oligomer has a sequence substantially corresponding to, or identical to, a sequence selected from SEQ ID NO:36 and SEQ ID NO:40.

Also provided by the present invention are detection probe oligomers, capture probe oligomers, and probe protection oligomers as described herein.

In another aspect, the present invention provides methods for determining the presence or absence of HEV in a sample using an oligomer combination as described herein. Such a method generally includes (1) contacting the sample with at least two oligomers for amplifying an HEV nucleic acid target region corresponding to an HEV target nucleic acid, where the oligomers include at least two amplification oligomers as described above; (2) performing an in vitro nucleic acid amplification reaction, where any HEV target nucleic acid present in the sample is used as a template for generating an amplification product; and (3) detecting the presence or absence of the amplification product, thereby determining the presence or absence of HEV in the sample. A detection method in accordance with the present invention typically further includes the step of obtaining the sample to be contacted with the at least two oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the HEV target nucleic acid from other components in the sample before the contacting step. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HEV nucleic acid and other sample components.

In some embodiments, an HEV target nucleic is selectively separated from other sample components by specifically hybridizing the HEV target nucleic acid to a capture probe oligomer. The capture probe oligomer comprises a target-hybridizing sequence configured to specifically hybridize to an HEV target sequence so as to form a target-sequence:capture-probe complex that is separated from sample components. Suitable capture probe target-hybridizing sequences include sequences substantially corresponding to, or identical to, a sequence selected from SEQ ID NO:2, SEQ ID NO:4, SEQ ID NO:6, and SEQ ID NO:42, including complements, DNA equivalents, and DNA/RNA chimerics thereof. In a preferred variation, the specific target capture binds the HEV target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to the HEV target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the capture probe has a sequence selected from SEQ ID NO:3, SEQ ID NO:7, and SEQ ID NO:43.

Target capture typically occurs in a solution phase mixture that contains one or more capture probe oligomers that hybridize specifically to the HEV target sequence under hybridizing conditions, usually at a temperature higher than the $T_m$ of the tail-sequence:immobilized-probe-sequence duplex. For embodiments comprising a capture probe tail, the HEV-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:HEV-target-sequence may be washed one or more times to further remove other sample components. Preferred embodiments use a particulate solid support, such as paramagnetic beads, so that particles with the attached HEV-target:capture-probe:mobilized-probe complex may be suspended in a washing solution and retrieved from the washing solution, preferably by using magnetic attraction. To limit the number of handling steps, the HEV target nucleic acid may be amplified by simply mixing the HEV target sequence in the complex on the support with amplification oligomers and proceeding with amplification steps.

Amplifying an HEV target sequence utilizes an in vitro amplification reaction using at least two amplification oligomers that flank a target region to be amplified. In particular embodiments, the target region to be amplified substantially corresponds to SEQ ID NO:1 from about nucleotide position 5230 to about nucleotide position 5379. Particularly suitable amplification oligomer combinations for amplification of these target regions are described herein (see, e.g., paragraphs [5]-[18] and [94]-[97], supra). Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., paragraphs [66] and [67], supra) and are readily used in accordance with the methods of the present invention.

For example, some amplification methods that use TMA amplification include the following steps. Briefly, the target nucleic acid that contains the sequence to be amplified is provided as single-stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above in paragraph [112] for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the HEV genomic RNA, and a probe will bind directly or indirectly to a sequence contained in the amplified product to indicate the presence of HEV nucleic acid in the tested sample.

Preferred embodiments of detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified HEV sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein (see, e.g., paragraphs [19], [20], and [38]-[40], supra). In some preferred embodiments of the method for detecting HEV sequences, such as in certain embodiments using transcription-mediated amplification (TMA), the detection probe is a linear chemiluminescently labeled probe, more preferably, a linear acridinium ester (AE) labeled probe.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

Examples of oligomers that are typically blocked at the 3' end—and which are particularly suitable in certain embodiments using transcription-mediated amplification—are promoter providers. As described previously, a promoter provider comprises first target-hybridizing region and, situated 5' to the first region, a second region comprising a promoter sequence for an RNA polymerase. The promoter provider oligonucleotide is modified to prevent the initiation of DNA synthesis from its 3'-terminus, such as by including a blocker group as discussed above.

Another example of typically 3'-blocked oligomers are terminating ("blocker") oligonucleotides, previously described above. A terminating oligomer is typically used in combination with, e.g., a promoter provider amplification oligomer, such as, for example, in certain embodiments described herein relating to transcription-mediated amplification (TMA). A terminating oligomer hybridizes to a sequence contained within the target nucleic acid in the vicinity of the 5'-end of the target region so as to "terminate" primer extension of a nascent nucleic acid that includes a priming oligonucleotide, thereby providing a defined 3'-end for the nascent nucleic acid strand.

Other embodiments using transcription-mediated amplification utilize a promoter primer, which comprises a first target-hybridizing region and, situated 5' to the first region, a second region comprising a promoter sequence for an RNA polymerase, but which is not modified to prevent the initiation of DNA synthesis from its 3'-terminus. In some embodiments, a promoter primer for use in accordance with the detection method comprises a target-hybridizing sequence having a sequence substantially corresponding to, or identical to, a sequence selected from SEQ ID NO:21, SEQ ID NO:22, SEQ ID NO:23, SEQ ID NO:24, SEQ ID NO:45, SEQ ID NO:46, SEQ ID NO:48, SEQ ID NO:49, SEQ ID NO:50, SEQ ID NO:51, SEQ ID NO:56. In certain variations of a promoter primer comprising a target-hybridizing sequence as in SEQ ID NO:56, the nucleobase at position 1 of SEQ ID NO:56 is guanine (G); in other variations, the promoter primer has degeneracy at position 1 of SEQ ID NO:56, such this position is occupied by either cytosine (C) or guanine (G) within a population of oligomers comprising SEQ ID NO:56. In more specific variations, a promoter primer for use in accordance with the detection method has the sequence shown in SEQ ID NO:7, SEQ ID NO:8, SEQ ID NO:9, SEQ ID NO:10, SEQ ID NO:11, SEQ ID NO:12, SEQ ID NO:14, SEQ ID NO:15, SEQ ID NO:17, SEQ ID NO:18, SEQ ID NO:19, or SEQ ID NO:20.

Assays for detection of the HEV nucleic acid may optionally include a non-HEV internal control (IC) nucleic acid that is amplified and detected in the same assay reaction mixtures by using amplification and detection oligomers specific for the IC sequence. IC nucleic acid sequences can be RNA template sequences (e.g., and in vitro transcript), synthetic nucleic acid sequences that are spiked into a sample or the IC nucleic acid sequences may be a cellular component. IC nucleic acid sequences that are cellular components can be from exogenous cellular sources or endogenous cellular sources relative to the specimen. In these instances, an internal control nucleic acid is co-amplified with the HEV nucleic acid in the amplification reaction mixtures. The internal control amplification product and the HEV target sequence amplification product can be detected independently. Two different internal control systems were employed in the procedures described below.

A first arrangement for internal control systems was useful for monitoring the integrity of amplification and detection reactions that employ paired sets of primers and an oligonucleotide probe that hybridized amplification product at a position between the primer binding sites, or the complements thereof. This arrangement was used in the assays described under Examples below. In a simple application, the internal control template nucleic acid can be distinguished from the analyte template nucleic acid at the sequence of bases serving as the probe binding site. These bases may be scrambled, replaced by an unrelated base sequence, or simply contain a sufficient number of point mutations to result in differential probe binding. In this way, nucleic acid products resulting from amplification of analyte nucleic acid can be detected by an analyte-specific probe, and not by an internal control-specific probe. Likewise, amplicons resulting from amplification of internal control nucleic acid can be detected by an internal control-specific probe, and not by an analyte-specific probe. This configuration allows that both analyte and internal control nucleic acid templates may be amplified using identical primers, or primer sets.

In certain embodiments, amplification and detection of a signal from the amplified IC sequence demonstrates that the assay reagents, conditions, and performance of assay steps were properly used in the assay if no signal is obtained for the intended target HEV nucleic acid (e.g., samples that test negative for HEV). An IC may also be used as an internal calibrator for the assay when a quantitative result is desired, i.e., the signal obtained from the IC amplification and detection is used to set a parameter used in an algorithm for quantitating the amount of HEV nucleic acid in a sample based on the signal obtained for an amplified HEV target sequence. ICs are also useful for monitoring the integrity of one or more steps in an assay. A preferred embodiment of a synthetic IC nucleic acid sequence is a randomized sequence that has been derived from a naturally occurring source (e.g., an HIV sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The primers and probe for the IC target sequence are configured and synthesized by using any well-known method provided that the primers and probe function for amplification of the IC target sequence and detection of the amplified IC sequence using substantially the same assay conditions used to amplify and detect the HEV target sequence. In preferred embodiments that include a target capture-based purification step, it is preferred that a target capture probe specific for the IC target be included in the assay in the target capture step so that the IC is treated in the assay in a manner analogous to that for the intended HEV analyte in all of the assay steps.

In certain embodiments of a method for determining the presence or absence of HEV in sample, the method further includes the use of a probe protection oligomer as described herein to adjust assay sensitivity.

Also provided by the subject invention is a reaction mixture for determining the presence or absence of an HEV target nucleic acid in a sample. A reaction mixture in accordance with the present invention at least comprises one or more of the following: an oligomer combination as described herein for amplification of an HEV target nucleic acid; a capture probe oligomer as described herein for purifying the HEV target nucleic acid; a detection probe oligomer as described herein for determining the presence or absence of an HEV amplification product; and a probe protection oligomer as described herein for detuning sensitivity of an assay for detecting the HEV target nucleic acid. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an HEV target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an amplification oligomer combination as described herein for amplification of an HEV target nucleic acid; a capture probe oligomer as described herein for purifying the HEV target nucleic acid; a detection probe oligomer as described herein for determining the presence or absence of an HEV amplification product; and a probe protection oligomer as described herein for detuning sensitivity of an assay for detecting the HEV target nucleic acid. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region of an HEV genome, or it may include amplification oligomers for multiple HEV target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Example 1

This example describes amplification reactions using various primer sets for amplification of an HEV target region. Table 2 below lists all the amplification oligomers used in this assay.

TABLE 2

| HEV Amplification Oligomers | |
|---|---|
| Class | SEQ ID NO: |
| nonT7 | 50 |
|  | 53 |
|  | 52 |
|  | 31 |
|  | 30 |

TABLE 2-continued

HEV Amplification Oligomers

| Class | SEQ ID NO: |
|---|---|
| | 29 |
| | 66 |
| | 65 |
| | 64 |
| | 62 |
| | 35 |
| | 34 |
| | 33 |
| | 61 |
| T7 | 17 |
| | 18 |
| | 19 |
| | 20 |
| | 9 |
| | 10 |
| | 11 |
| | 12 |
| | 15 |
| | 14 |

Each possible combination of the T7 and nonT7 primers listed in Table 2 were tested. Primers were tested in a transcription-mediated amplification (TMA) reaction using an HEV in vitro transcript (IVT) at 15 and 0 copies/reaction. Transcription mediated amplification (TMA) reactions were carried out essentially as described by Kacian et al., in U.S. Pat. No. 5,399,491, the disclosure of this U.S. patent having been incorporated by reference hereinabove. Amplification reactions were conducted for various primer combinations using about 5 to 10 pmoles per reaction of each T7 primer and nonT7 primer. Amplification products were detected by hybridization protection assay (HPA) using an AE-labeled detection probe (having the nucleobase sequence shown in SEQ ID NO:67). Signal-to-noise ratios were calculated for each primer pair by dividing the RLU value observed at 15 copies of HEV IVT by the background RLU value observed at 0 copies of HEV IVT. The results are shown in Table 3 below.

Primer pairs that demonstrated a signal-to-background ratio of at least 10 or more were considered to be successful for amplification of HEV target nucleic acid to at least as low as 15 copies per reaction, while those pairs demonstrating a ratio of below 10 were considered to be unsuccessful. Ratios over 10 are shown in bold in Table 3.

Example 2

This example describes HEV amplification and detection assays performed using different oligomer combinations. Reagents, oligonucleotides, and samples used in these experiments are listed in Tables 4-6 below.

TABLE 4

HEV Assay Reagents

| Reagent Name | Description |
|---|---|
| Internal Control Reagent | A HEPES buffered solution containing detergent and an RNA transcript. |
| Target Capture Reagent | A HEPES buffered solution containing detergent, capture oligonucleotides and magnetic microparticles. |
| Amplification Reagent | Primers, dNTPs, NTPs and co-factors in TRIS buffered solution containing ProClin 300 as preservative. |
| Enzyme Reagent | MMLV Reverse Transcriptase and T7 RNA Polymerase in HEPES/TRIS buffered solution containing 0.05% sodium azide as preservative. |
| Probe Reagent | Chemiluminescent oligonucleotide probes in succinate buffered solution containing detergent. |
| HEV Negative Calibrator | A HEPES buffered solution containing detergent. |
| HEV Positive Calibrator | A HEPES buffered solution containing detergent and an HEV RNA transcript. |

TABLE 5

HEV-specific Oligonucleotides

| Class | SEQ ID NO: |
|---|---|
| Target Capture Oligo | 74 |
| Target Capture Oligo | 76 |
| Target Capture Oligo | 43 |
| Target Capture Oligo | 3 |

TABLE 3

Signal-to-Noise Ratio of HEV T7/nonT7 Primer Pairs

| | | nonT7† | | | | | | | | | | | | |
|---|---|---|---|---|---|---|---|---|---|---|---|---|---|---|
| | | 66 | 65 | 64 | 62 | 61 | 53 | 52 | 50 | 35 | 34 | 33 | 31 | 30 | 29 |
| T7† | 9 | 898.1 | 896.5 | 487 | 802.2 | 599.2 | 1.6 | 0.9 | 75 | 916.5 | 361.1 | 956.7 | 910 | 943.3 | 1010 |
| | 10 | 1183.7 | 974.4 | 1078.3 | 1023.6 | 1097.1 | 5.2 | 2.9 | 289.1 | 994.3 | 971.8 | 282.3 | 1102.3 | 22.9 | 907 |
| | 11 | 1252.1 | 1286.2 | 933.6 | 1023 | 709.5 | 12 | 4 | 314.6 | 1013.3 | 1139.3 | 1044.1 | 308 | 14.9 | 906.3 |
| | 12 | 944.6 | 980.1 | 1007.9 | 1061.4 | 595.1 | 675.9 | 26 | 1026.2 | 966.6 | 942.8 | 927.6 | 945.7 | 953.4 | 854.5 |
| | 14 | 3204.9 | 3120.2 | 2855.6 | 2919.1 | 2576.4 | 1001.5 | 1.6 | 891.9 | 2282.4 | 2574.2 | 2809.9 | 1800.1 | 227.1 | 679.9 |
| | 15 | 1545.2 | 2074.8 | 2578.8 | 1361.2 | 2639.7 | 252.3 | 2.4 | 433.5 | 1253.3 | 2690.7 | 2161.8 | 313.7 | 1782.1 | 1058.6 |
| | 17 | 273.8 | 429.2 | 498 | 220.6 | 281.2 | 0.7 | 3.3 | 8.5 | 135.4 | 222.5 | 65.9 | 201.8 | 1.7 | 233.9 |
| | 18 | 914 | 445.7 | 896.2 | 906.3 | 780 | 0.9 | 0.9 | 1.1 | 809.1 | 716 | 171.2 | 1377.4 | 3 | 1191.2 |
| | 19 | 406.4 | 983.8 | 1135.8 | 750.1 | 703.8 | 1.1 | 1 | 1.6 | 981.4 | 836.6 | 496.4 | 1512.5 | 135.6 | 1075 |
| | 20 | 1225.7 | 1048.4 | 898.3 | 752.8 | 786.5 | 124.9 | 1 | 345.5 | 886.1 | 892.5 | 737.5 | 1249.7 | 932.2 | 1197.9 |

†NonT7 primer designations are the SEQ ID NOs, as listed in Table 2, supra. Similarly, T7 primer designations are the SEQ ID NOs, as listed in Table 2, supra.

TABLE 5-continued

HEV-specific Oligonucleotides

| Class | SEQ ID NO: |
| --- | --- |
| Target Capture Oligo | 7 |
| Non-T7 Primer | 29 |
| Non-T7 Primer | 66 |
| Non-T7 Primer | 65 |
| Non-T7 Primer | 64 |
| Non-T7 Primer | 62 |
| T7 Primer | 12 |
| T7 Primer | 15 |
| AE Labeled Probe | 67 |
| AE Labeled Probe | 55 |
| AE Labeled Probe | 55 |
| AE Labeled Probe | 55 |

TABLE 6

Samples Tested

| Sample | Description |
| --- | --- |
| Positive Sample | HEV In Vitro Transcript (IVT) in IC buffer |
| Negative Sample | HEV negative serum |

Steps Performed

Principles of the Procedure

The HEV assay involved three main steps, which take place in a single tube: sample preparation; HEV RNA target amplification by Transcription-Mediated Amplification (TMA); and detection of the amplification products (amplicon) by the Hybridization Protection Assay (HPA).

During sample preparation, RNA was isolated from specimens via the use of target capture. The specimen was treated with a detergent to solubilize the viral particles, denature proteins and release viral genomic RNA. Oligonucleotides ("capture oligonucleotides") that are homologous to highly conserved regions of HEV were hybridized to the HEV RNA target, if present, in the test specimen. The hybridized target was then captured onto magnetic microparticles that were separated from the specimen in a magnetic field. Wash steps were utilized to remove extraneous components from the reaction tube. Magnetic separation and wash steps were performed with a target capture system.

Target amplification occurred via TMA, which is a transcription-based nucleic acid amplification method that utilizes two enzymes, MMLV reverse transcriptase and T7 RNA polymerase. The reverse transcriptase was used to generate a DNA copy (containing a promoter sequence for T7 RNA polymerase) of the target RNA sequence. The T7 RNA polymerase produces multiple copies of RNA amplicon from the DNA copy template. The HEV assay utilized the TMA method to amplify regions of HEV RNA.

Detection was achieved by HPA using single-stranded nucleic acid probes with chemiluminescent labels that are complementary to the amplicon. The labeled nucleic acid probes hybridize specifically to the amplicon. The Selection Reagent differentiated between hybridized and unhybridized probes by inactivating the label on unhybridized probes. During the detection step, the chemiluminescent signal produced by the hybridized probe was measured by a luminometer and was reported as Relative Light Units (RLU).

Internal Control was added to each test specimen and assay calibrator via the working Target Capture Reagent. The Internal Control (IC) in the HEV assay controlled for specimen processing, amplification and detection steps. Internal Control signal was discriminated from the HEV signal by the differential kinetics of light emission from probes with different labels. Internal Control-specific amplicon was detected using a probe with rapid emission of light (flasher signal). Amplicon specific to HEV was detected using probes with relatively slower kinetics of light emission (glower signal). The Dual Kinetic Assay (DKA) is a method used to differentiate between the signals from flasher and glower labels.

Order of Steps

Target Capture: Nucleic acids underwent specimen processing and target capture prior to amplification essentially according to the procedures disclosed in published International Patent Application No. PCT/US2000/18685, except that templates were captured using Hepatitis E virus target capture oligonucleotides having the sequences given herein. Notably, capture oligonucleotides do not participate in the amplification or detection reactions of the assay. Virus-containing samples were combined with a target capture reagent to facilitate nucleic acid release and hybridization to capture oligonucleotides disposed on magnetic beads. Incubation were performed to capture HEV nucleic acids from the sample. Following the incubation, the magnetic beads and any capture target nucleic acids were transferred to a magnetic wash station for 10-20 min for a wash step. Captured target nucleic acids were then assayed in an amplification reaction.

Transcription mediated amplification (TMA) reactions were carried out essentially as described in Example 1. Isolated target nucleic acids were combined with primers in amplification reagent (Table 2) heated to 60° C. for 10 minutes and then cooled to 42° C. to facilitate primer annealing. Enzyme reagent was then added to the mixtures and the amplification reactions were carried out, as will be familiar to those having an ordinary level of skill in the art.

Detection: After a one hour incubation at 42° C., the amplification reaction volumes were subjected to hybridization assays employing probes internally labeled with a chemiluminescent compound using techniques familiar to those having an ordinary level of skill in the art, and then used in amounts equivalent to about 2 E+06 to about 6 E+06 RLU for each probe in the hybridization reaction. (See e.g., U.S. Pat. Nos. 5,585,481 and 5,639,604, the disclosures of these patents are incorporated by reference). Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label linked to unhybridized probe, and cooled briefly to room temperature (i.e., 15-30° C.) prior to reading the hybridization signal. Chemiluminescence due to hybridized probe in each sample was assayed using commercially available instrumentation (Gen-Probe Incorporated; San Diego, Calif.) configured for injection of 1 mM nitric acid and 0.1% (v/v) hydrogen peroxide, followed by injection of a solution containing 1 N sodium hydroxide. Results for the chemiluminescent reactions were measured in relative light units (RLU). In this procedure, the signal/noise value corresponded to the chemiluminescent signal (measured in RLU) generated by label associated with specifically hybridized probe divided by a background signal measured in the absence of a target nucleic acid.

Results and Discussion

Experiment I—Combining Amplification Systems

The objective was to test pairs of T7 and non-T7, as well as some individually, in order to confirm which of the different primer combinations exhibited better performance and which individual primers functionally performed the best. Target capture reactions were performed using SEQ ID NO:76 as a target capture oligomer. Detection reactions were performed using SEQ ID NO:67 as an AE-labeled detection probe oligomer. Amplification oligomer combinations are shown in Table 7, below. After determining SEQ ID NO:29+SEQ ID NO:65 and SEQ ID NO:12 primers work best in previous experiments, much of this experiment focused on these particular primers. Increasing the concentrations of some primers were also tested to evaluate performance and function in the system. Panels at 20 copies/mL HEV IVT (8 replicates) and BI0052 negative serum (2 replicates) were tested for each amplification system.

TABLE 7

Experimental Design for Experiment I

| Amp Systems | Non-T7 Primer (SEQ ID NO) | T7 Primer (SEQ ID NO) |
|---|---|---|
| 1 | 29 | 12 |
| 2 | 65 | 12 |
| 3 | 29 + 65 | 12 |
| 4 | 29 + 65 | 15 |
| 5 | 29 + 65 | 12 + 15 |
| 6 | 29 + 65 | 12 + 15 |
| 7 | 29 + 65 | 12 + 15 |
| 8 | 29 + 65 | 12 + 15 |
| 9 | 29 + 65 | 12 + 15 |
| 10 | 29 | 12 + 15 |
| 11 | 66 | 12 + 15 |
| 12 | 65 | 12 + 15 |
| 13 | 64 | 12 + 15 |
| 14 | 62 | 12 + 15 |
| 15 | 65 | 15 |
| 16 | 65 | 15 |
| 17 | 65 | 15 |

*In all Amp Systems except for 6, 7, 8, 9, 16 & 17, the Non-T7 Primers and the T7 Primers were used at roughly the same concentrations to one another. In Amp Systems 6, 7, 8, 9, 16 & 17 the following primer members were used at twice the concentration of the other primers in the reaction: 65, 29, 12, 15, 65 and 15, respectively.

Table 8 shows a summary for Experiment I. When paired with SEQ ID NO:12, SEQ ID NO:65 performed better than SEQ ID NO:29, as shown in the higher mean RLU and lower % CV values (Amp systems 1 and 2). When paired with SEQ ID NO:29+SEQ ID NO:65, SEQ ID NO:12 performed better than SEQ ID NO:15, as shown in the higher mean RLU and lower % CV values (Amp systems 3 and 4). As seen with Amp system 5, adding SEQ ID NO:15 improved RLU signal compared to Amp system 3. Keeping SEQ ID NO:29+SEQ ID NO:65 both at 5 pmol/reaction showed better RLU and % CV performance (Amp system 5) than increasing SEQ ID NO:65 to 10 pmol/reaction in Amp system 6. When comparing Amp systems 8 and 9, increasing SEQ ID NO:12 from 5 to 10 pmol/reaction showed better performance than increasing SEQ ID NO:15. Amp systems 10 through 14 compared which non-T7 would perform with higher RLUs and low % CVs. Based on the criteria, SEQ ID NO:66 and SEQ ID NO:64 showed the highest RLUs and lowest % CVs. Amp systems 15 through 17 increased the concentration from 5 to 10 pmol/reaction of either the non-T7 or T7 in the system. Comparing Amp systems 15 and 16 these data show that increasing SEQ ID NO:65 improved performance (Amp system 16) while, on the other hand, increasing SEQ ID NO:15 decreased performance (Amp system 17).

TABLE 8

Summary of Results for Experiment I

| System | Panel | RLU Mean | RLU SD | RLU % CV | S/CO | % R |
|---|---|---|---|---|---|---|
| Amp 1 | 20 c/mL | 1,035,254 | 60,059 | 5.80 | 105.76 | 100 |
| Amp 2 | 20 c/mL | 1,367,829 | 17,738 | 1.30 | 139.73 | 100 |
| Amp 3 | 20 c/mL | 1,265,443 | 40,365 | 3.19 | 129.27 | 100 |
| Amp 4 | 20 c/mL | 354,741 | 412,106 | 116.17 | 36.24 | 100 |
| Amp 5 | 20 c/mL | 1,307,112 | 39,148 | 2.99 | 133.53 | 100 |
| Amp 6 | 20 c/mL | 1,138,545 | 346,932 | 30.47 | 116.31 | 100 |
| Amp 7 | 20 c/mL | 1,157,461 | 23,540 | 2.03 | 118.24 | 100 |
| Amp 8 | 20 c/mL | 1,315,063 | 11,663 | 0.89 | 134.34 | 100 |
| Amp 9 | 20 c/mL | 993,828 | 353,189 | 35.54 | 101.53 | 100 |
| Amp 10 | 20 c/mL | 1,110,792 | 102,117 | 9.19 | 113.47 | 100 |
| Amp 11 | 20 c/mL | 1,377,343 | 45,052 | 3.27 | 140.70 | 100 |
| Amp 12 | 20 c/mL | 1,343,435 | 66,431 | 4.94 | 137.24 | 100 |
| Amp 13 | 20 c/mL | 1,372,134 | 48,909 | 3.56 | 140.17 | 100 |
| Amp 14 | 20 c/mL | 1,342,071 | 92,993 | 6.93 | 137.10 | 100 |
| Amp 15 | 20 c/mL | 606,324 | 424,338 | 69.99 | 61.94 | 100 |
| Amp 16 | 20 c/mL | 1,089,242 | 259,106 | 23.79 | 111.27 | 100 |
| Amp 17 | 20 c/mL | 395,478 | 164,783 | 41.67 | 40.40 | 100 |

RLU = Relative Light Units; SD = Standard Deviation; CV = Coefficient of Variation; S/CO = Signal to Cutoff Ratio; % R = % Reactivity.

Experiment II—Confirming the Best Performing Primer Pair Combination

The objective was to test pairs of T7 and non-T7 and different primer combinations in the amplification reagent. Panel at 20 c/mL HEV IVT was tested in 5 replicates for each amplification system.

Table 9 shows the experimental design. All conditions stayed the same except for the amplification systems tested. Target capture was performed using SEQ ID NO:76 and detection was performed using an AE-labeled SEQ ID NO:67 as a detection probe. As shown in Experiment I, Amp system 1 showed good performance, and that was set as a control. Amp systems 2 through 4 tested how each non-T7 compared to each other when only paired with SEQ ID NO:15. Since SEQ ID NO:66, SEQ ID NO:64, and SEQ ID NO:62 showed good RLU and % CV performance in Experiment I, each these non-T7s were tested in the primer pairing combinations shown in Amp systems 5 through 7.

TABLE 9

Experimental Design for Experiment II

| Amp Systems | Non-T7 (SEQ ID NO) | T7 (SEQ ID NO) |
|---|---|---|
| 1 | 29 + 65 | 12 + 15 |
| 2 | 66 | 15 |
| 3 | 64 | 15 |
| 4 | 62 | 15 |
| 5 | 29 + 66 | 12 + 15 |
| 6 | 29 + 64 | 12 + 15 |
| 7 | 29 + 62 | 12 + 15 |

Table 10 shows a summary for Experiment II. When comparing Amp systems 2 through 4, SEQ ID NO:64 showed best performance in higher mean RLU compared to SEQ ID NO:66 and SEQ ID NO:62. When comparing Amp systems 1 and 6, SEQ ID NO:29 paired with SEQ ID NO:64 performed better than SEQ ID NO:29+SEQ ID NO:65. Even though Amp system 5 showed the highest RLU performance when compared with Amp systems 6 and 7, Amp system 6 was chosen for further study based on sequence alignment.

TABLE 10

Summary of Results for Experiment II

| System | Panel | RLU Mean | RLU SD | RLU % CV | S/CO | % R |
|---|---|---|---|---|---|---|
| Amp 1 | 20 c/mL | 1,054,954 | 455,280 | 43.16 | 107.77 | 100 |
| Amp 2 | 20 c/mL | 108,457 | 79,457 | 73.26 | 11.08 | 100 |
| Amp 3 | 20 c/mL | 386,281 | 308,958 | 79.98 | 39.46 | 100 |
| Amp 4 | 20 c/mL | 166,652 | 96,680 | 58.01 | 17.02 | 100 |
| Amp 5 | 20 c/mL | 1,251,195 | 73,533 | 5.88 | 127.82 | 100 |
| Amp 6 | 20 c/mL | 1,219,780 | 130,591 | 10.71 | 124.61 | 100 |
| Amp 7 | 20 c/mL | 1,242,616 | 54,910 | 4.42 | 126.94 | 100 |

RLU = Relative Light Units; SD = Standard Deviation; CV = Coefficient of Variation; S/CO = Signal to Cutoff Ratio; % R = % Reactivity.

Experiment III—Screening New Probe Pairs

The objective was to test new probe oligo pairs and evaluate the performance. Each of the probes was also tested individually to evaluate performance. Panel at 0 (IC buffer only) and 1,000 copies/mL HEV IVT were tested as negative and positive calibrators, respectively, of the assay. Panel at 20 copies/mL of HEV IVT and BI0052 negative serum were tested as samples at 7 replicates each. Each panel type was tested for each probe condition.

Table 11 shows the experimental design. All conditions stayed the same except for the 7 probe systems tested. Internal control (IC) probe was also added to each of the 7 probes listed in the table.

TABLE 11

Experiments Design for Experiment III

| Probe# | Probe‡ | Probe (RLU/rxn) | TCOs in TCR | Primers in Amp* |
|---|---|---|---|---|
| Probe 1 | SEQ ID NO: 67 | 2.00E+06 | SEQ ID NO: 43 | SEQ ID NO: 29 + SEQ ID NO: 12 + |
| Probe 2 | SEQ ID NO: 55 [8, 9] | 3.00E+06 | SEQ ID NO: 3 | SEQ ID NO: 64  SEQ ID NO: 15 |
| Probe 3 | SEQ ID NO: 55 [10, 11] | 3.00E+06 | SEQ ID NO: 7 | |
| Probe 4 | SEQ ID NO: 55 [12, 13] | 6.00E+06 | | |
| Probe 5 | SEQ ID NO: 67 | 2.00E+06 | | |
| | SEQ ID NO: 55 [12, 13] | 6.00E+06 | | |
| Probe 6 | SEQ ID NO: 55 [8, 9] | 3.00E+06 | | |
| | SEQ ID NO: 55 [12, 13] | 6.00E+06 | | |
| Probe 7 | SEQ ID NO: 55 [10, 11] | 3.00E+06 | | |
| | SEQ ID NO: 55 [12, 13] | 6.00E+06 | | |
| IC Probe added to Probes #1-7 | SEQ ID NO: 78-PPO Hybrid | 1.00E+06 | | |

‡The [#, #] designation refers to the nucleobase residues (counting from 5' to 3') between which a chemiluminescent label was located for SEQ ID NO: 55.
*SEQ ID NO: 64 was tested at 2X the concentration per reaction compared to each of SEQ ID NOs: 12, 15 & 29.

Table 12 shows a summary for Experiment III. When looking at the probe reagents containing probe pairs (Probes 5, 6, and 7), probes 5 and 6 showed low background (low analyte RLU in the Negative Calibrator and BI0052 negative serum), and high analyte RLU signal in the Positive Calibrator and HEV IVT at 20 c/mL. Probe 7 also showed a similar result. Of the three probes (Probes 5, 6, and 7), Probe 5 had the highest analyte RLU signal in the positive samples. For the individual probe performance (Probes 1 through 4), SEQ ID NO:67 showed the highest analyte RLU signal in the positive samples, which relatively high background signal in the negative samples.

TABLE 12

Summary of Results for Experiment III - IC RLU and analyte RLU

| Condition | Panel | IC RLU | | | | Analyte RLU | | | |
|---|---|---|---|---|---|---|---|---|---|
| | | Mean | SD | % CV | 95% CI | Mean | SD | % CV | 95% CI |
| Probe1 | Neg Cal | 134,234 | 6,423 | 4.78 | | 454 | 468 | 103.06 | |
| Probe1 | Pos Cal 1k c/mL | 134,264 | 22,989 | 17 | | 1,207,525 | 10,587 | 0.88 | |
| Probe1 | 20 c/mL HEV IVT | 134,667 | 25,652 | 19.05 | 19,003 | 1,129,086 | 121,191 | 10.73 | 89,778 |
| Probe1 | BI0052 BN 593600 | 140,531 | 12,824 | 9.13 | 9,500 | 626 | 756 | 120.61 | 560 |
| Probe2 | Neg Cal | 130,780 | 3,363 | 2.57 | | 595 | 217 | 36.46 | |
| Probe2 | Pos Cal 1k c/mL | 130,740 | 12,322 | 9 | | 1,209,761 | 16,267 | 1.34 | |
| Probe2 | 20 c/mL HEV IVT | 178,999 | 26,435 | 14.77 | 19,583 | 855,109 | 371,340 | 43.43 | 275,087 |
| Probe2 | BI0052 BN 593600 | 126,281 | 9,860 | 7.81 | 7,304 | 916 | 265 | 28.93 | 196 |
| Probe3 | Neg Cal | 134,046 | 4,495 | 3.35 | | 144 | 250 | 173.21 | |
| Probe3 | Pos Cal 1k c/mL | 134,061 | 9,411 | 7 | | 854,435 | 10,650 | 1.25 | |

TABLE 12-continued

Summary of Results for Experiment III - IC RLU and analyte RLU

| | | IC RLU | | | | Analyte RLU | | | |
|---|---|---|---|---|---|---|---|---|---|
| Condition | Panel | Mean | SD | % CV | 95% CI | Mean | SD | % CV | 95% CI |
| Probe3 | 20 c/mL HEV IVT | 132,559 | 18,420 | 13.90 | 13,645 | 649,395 | 287,954 | 44.34 | 213,316 |
| Probe3 | BI0052 BN 593600 | 134,791 | 9,170 | 6.80 | 6,793 | 432 | 609 | 140.93 | 451 |
| Probe4 | Neg Cal | 127,697 | 7,878 | 6.17 | | 4,580 | 376 | 8.21 | |
| Probe4 | Pos Cal 1k c/mL | 127,584 | 1,216 | 1 | | 379,813 | 8,359 | 2.20 | |
| Probe4 | 20 c/mL HEV IVT | 135,488 | 2,617 | 1.93 | 1,939 | 160,017 | 74,978 | 46.86 | 55,543 |
| Probe4 | BI0052 BN 593600 | 129,564 | 5,516 | 4.26 | 4,086 | 4,189 | 461 | 11.01 | 342 |
| Probe5 | Neg Cal | 135,336 | 2,380 | 1.76 | | 5,778 | 1,312 | 22.70 | |
| Probe5 | Pos Cal 1k c/mL | 135,756 | 5,561 | 4 | | 1,585,647 | 9,575 | 0.60 | |
| Probe5 | 20 c/mL HEV IVT | 136,693 | 9,838 | 7.20 | 7,288 | 1,131,831 | 490,936 | 43.38 | 363,684 |
| Probe5 | BI0052 BN 593600 | 129,554 | 10,328 | 7.97 | 7,651 | 6,440 | 1,997 | 31.01 | 1,479 |
| Probe6 | Neg Cal | 135,671 | 4,178 | 3.08 | | 6,024 | 488 | 8.11 | |
| Probe6 | Pos Cal 1k c/mL | 135,139 | 8,626 | 6 | | 1,468,351 | 32,266 | 2.20 | |
| Probe6 | 20 c/mL HEV IVT | 169,229 | 32,044 | 18.94 | 23,738 | 787,965 | 610,399 | 77.47 | 452,181 |
| Probe6 | BI0052 BN 593600 | 141,381 | 6,476 | 4.58 | 4,797 | 5,965 | 901 | 15.11 | 668 |
| Probe7 | Neg Cal | 131,353 | 1,086 | 0.83 | | 6,194 | 415 | 6.71 | |
| Probe7 | Pos Cal 1k c/mL | 131,669 | 15,624 | 12 | | 1,200,190 | 17,730 | 1.48 | |
| Probe7 | 20 c/mL HEV IVT | 189,382 | 12,230 | 6.46 | 9,060 | 1,062,012 | 44,717 | 4.21 | 33,126 |
| Probe7 | BI0052 BN 593600 | 139,499 | 9,591 | 6.88 | 7,105 | 5,746 | 694 | 12.09 | 514 |

RLU = Relative Light Units;
SD = Standard Deviation;
CV = Coefficient of Variation;
CI = Confidence Interval Table 13 shows a summary of the mean analyte S/CO values, including the reactivity, and validity, for Experiment III.

TABLE 13

Summary of Results for Experiment III - Analyte S/CO, Reactivity, and Validity

| | | Analyte S/CO | | | | | | | | |
|---|---|---|---|---|---|---|---|---|---|---|
| Condition | Panel | Mean | SD | % CV | 95% CI | NR | R | Invalid | Valid | % R |
| Probe1 | Neg Cal | 0.01 | 0.01 | 103.06 | | | | 0 | | |
| Probe1 | Pos Cal 1k c/mL | 32.92 | 0.29 | 0.88 | | | | 0 | | |
| Probe1 | 20 c/mL HEV IVT | 30.78 | 3.30 | 10.73 | 2.45 | 0 | 7 | 0 | 7 | 100 |
| Probe1 | BI0052 BN 593600 | 0.02 | 0.02 | 120.61 | 0.02 | 7 | 0 | 0 | 7 | 0 |
| Probe2 | Neg Cal | 0.02 | 0.01 | 36.46 | | | | 0 | | |
| Probe2 | Pos Cal 1k c/mL | 32.80 | 0.44 | 1.34 | | | | 0 | | |
| Probe2 | 20 c/mL HEV IVT | 23.18 | 10.07 | 43.43 | 7.46 | 1 | 6 | 0 | 7 | 86 |
| Probe2 | BI0052 BN 593600 | 0.02 | 0.01 | 28.93 | 0.01 | 7 | 0 | 0 | 7 | 0 |
| Probe3 | Neg Cal | 0.01 | 0.01 | 173.21 | | | | 0 | | |
| Probe3 | Pos Cal 1k c/mL | 33.15 | 0.41 | 1.25 | | | | 0 | | |
| Probe3 | 20 c/mL HEV IVT | 25.19 | 11.17 | 44.34 | 8.28 | 1 | 6 | 0 | 7 | 86 |
| Probe3 | BI0052 BN 593600 | 0.02 | 0.02 | 140.93 | 0.02 | 7 | 0 | 0 | 7 | 0 |
| Probe4 | Neg Cal | 1.00 | 0.08 | 8.21 | | | | 3 | | |
| Probe4 | Pos Cal 1k c/mL | 82.93 | 1.83 | 2.20 | | | | 3 | | |
| Probe4 | 20 c/mL HEV IVT | 34.94 | 16.37 | 46.86 | 12.13 | 0 | 0 | 7 | 0 | #DIV/0! |
| Probe4 | BI0052 BN 593600 | 0.91 | 0.10 | 11.01 | 0.07 | 0 | 0 | 7 | 0 | #DIV/0! |
| Probe5 | Neg Cal | 0.11 | 0.02 | 22.70 | | | | 0 | | |
| Probe5 | Pos Cal 1k c/mL | 29.72 | 0.18 | 0.60 | | | | 0 | | |
| Probe5 | 20 c/mL HEV IVT | 21.22 | 9.20 | 43.38 | 6.82 | 0 | 7 | 0 | 7 | 100 |
| Probe5 | BI0052 BN 593600 | 0.12 | 0.04 | 31.01 | 0.03 | 7 | 0 | 0 | 7 | 0 |
| Probe6 | Neg Cal | 0.12 | 0.01 | 8.11 | | | | 0 | | |
| Probe6 | Pos Cal 1k c/mL | 29.32 | 0.64 | 2.20 | | | | 0 | | |
| Probe6 | 20 c/mL HEV IVT | 15.74 | 12.19 | 77.47 | 9.03 | 1 | 6 | 0 | 7 | 86 |
| Probe6 | BI0052 BN 593600 | 0.12 | 0.02 | 15.11 | 0.01 | 7 | 0 | 0 | 7 | 0 |
| Probe7 | Neg Cal | 0.15 | 0.01 | 6.71 | | | | 0 | | |

TABLE 13-continued

Summary of Results for Experiment III - Analyte S/CO, Reactivity, and Validity

| | | Analyte S/CO | | | | | | | | |
|---|---|---|---|---|---|---|---|---|---|---|
| Condition | Panel | Mean | SD | % CV | 95% CI | NR | R | Invalid | Valid | % R |
| Probe7 | Pos Cal 1k c/mL | 28.44 | 0.42 | 1.48 | | | | 0 | | |
| Probe7 | 20 c/mL HEV IVT | 25.17 | 1.06 | 4.21 | 0.78 | 0 | 7 | 0 | 7 | 100 |
| Probe7 | BI0052 BN 593600 | 0.14 | 0.02 | 12.09 | 0.01 | 7 | 0 | 0 | 7 | 0 |

S/CO = Signal to cutoff ratio;
SD = Standard Deviation;
CV = Coefficient of Variation;
CI = Confidence Interval;
NR = Non-Reactive;
R = Reactive;
% R = % Reactivity Example 3

This example describes evaluation of analytical sensitivity, cross-reactivity, specificity, and further probe formulation for an HEV amplification and detection assay. Reagents are as previously described in Example 2. Oligonucleotides and samples used in these experiments are listed in Tables 14 and 15 below.

TABLE 14

HEV-specific Oligonucleotides and Internal Control Flasher Probe and PPO

| SEQ ID NO | Class[1] | Sequence (5'-3') |
|---|---|---|
| 64 | Non-T7 Primers | TGCTGCCCGCGCCAC |
| 29 | Non-T7 Primers | CCGGCGGTGGTTTCT |
| 37 | AE Labeled Probes | gaccggguugauucuC |
| 67 | AE Labeled Probes | ugauucucagcccuucgC |
| 71 | AE Labeled Probes | ugauugucagcccuucgC |
| 36 | Probe Protection Oligos | GAAGGGCTGAGAATCA |
| 40 | Probe Protection Oligos | GAGAATCAACCCGGT |
| 12 | T7 Promoter Primers | AATTTAATACGACTCACTATAGGGAGAAGGGGTTGGTTGGATGAATATAGGGGA |
| 15 | T7 Promoter Primers | AATTTAATACGACTCACTATAGGGAGAGGGCGAAGGGGTTGGTTGGATGAA |
| 3 | Capture Oligos | aagacauguuauucauuccacccTTTAAAAAAAAAAAAAAAAAAAAAAAAAAA |
| 7 | Capture Oligos | aagacauguuauucauucuacccTTTAAAAAAAAAAAAAAAAAAAAAAAAAAA |
| 43 | Capture Oligos | gaggggcgcugggacuggucgTTTAAAAAAAAAAAAAAAAAAAAAAAAAAA |

TABLE 14-continued

HEV-specific Oligonucleotides and Internal Control Flasher Probe and PPO

| SEQ ID NO | Class[1] | Sequence (5'-3') |
|---|---|---|
| 78 | AE Labeled Probes | ccacaagcuuagaagauagagagG |
| 79 | Probe Protection Oligos | CTATCTTCTAAGCTTG |

[1]Lower case = methoxy RNA; Upper case = DNA

TABLE 15

| | | Samples Tested | | |
|---|---|---|---|---|
| Sample | Description | | Source | Matrix |
| HEV Standard (6329/10) | 1st World Health Organization International Standard for Hepatitis E Virus RNA Nucleic Acid Amplification Techniques (NAT)-Based Assays | | PEI (Paul Ehrlich Institute) | Lyophilized plasma |
| HEV RNA transcripts | HEV genotypes 1-4 | | In-house | IC buffer |
| HEV negative plasma | Frozen plasma, 2100 unique donors | | BocaBiolistics | plasma |

Steps Performed

Assay steps were performed as described in Example 2.

Results and Discussion

Analytical Sensitivity

Analytical sensitivity of the HEV assay on was determined using the 1st World Health Organization (WHO) International Standard (IS) for HEV RNA Nucleic Acid Amplification Techniques (NAT)-Based Assays (PEI code 6329/10). The WHO IS is based on HEV genotype 3a derived from a clinical isolate (GenBank accession number AB630970) first obtained by the Paul Ehrlich Institute (Langen, Germany) from the Hokkaido Red Cross [part of The Japanese Red Cross (JRC)].

The sensitivity was determined to be 8.4 International Unit (IU)/mL at 95% detection level for HEV WHO IS.

TABLE 16

Analytical Sensitivity with the WHO Standard for HEV

| International Units/mL (n = 81) | Percent Reactivity of HEV WHO IS |
|---|---|
| 90 | 100 |
| 30 | 100 |
| 10 | 91 |
| 3 | 52 |
| 1 | 22 |
| 0 | 0 |

| Detection Probability by Probit Analysis* | Limit of Detection in IU/mL |
|---|---|
| 95% LOD (95% fiducial limits) | 8.4 (6.3-12.8) |
| 50% LOD (95% fiducial limits) | 1.7 (1.4-2.1) |

*Using SAS 9.2 Probit normal model

Analytical sensitivity of HEV Assay among various HEV genotype IVTs.

RNA IVTs were prepared for each of the major known HEV genotypes 1-4, including three sub-genotypes for HEV-3, namely HEV-3a, HEV-3b and HEV-3f. HEV-3a IVT is used as the HEV assay Positive Calibrator. In addition, RNA IVT was also made for a putative HEV genotype 6. The sensitivity for each of the major HEV genotype/sub-genotype IVT was determined to be in the range of 10-19 c/mL at 95% detection level. The exception is with the putative HEV genotype 6 in which the sensitivity of the HEV Assay is about 5 times lower compared to the average sensitivity of HEV genotype 1-4 IVTs. The lower detection of the putative HEV genotype 6 strain in the HEV assay is mitigated by the fact that there is only one strain (wb-JOY_06; GenBank accession number AB602441) associated with the putative genotype 6, that it was found in a single wild boar in Japan, and that it has not been associated with any known human HEV cases (Takahashi M et al., *J. Gen. Virol.* 92:902-908, 2011).

TABLE 17

Analytical Sensitivity among HEV Genotype IVTs

| Copies/mL (n = 81) | Percent Reactivity of Genotype[a] IVTs | | | | | | |
|---|---|---|---|---|---|---|---|
| | 1 | 2 | 3a | 3b | 3f | 4c | 6[b] |
| 90 | 100 | 100 | 100 | 100 | 100 | 100 | 98 |
| 30 | 100 | 100 | 100 | 99 | 100 | 98 | 88 |
| 10 | 94 | 94 | 91 | 94 | 95 | 90 | 46 |
| 3 | 44 | 49 | 52 | 42 | 60 | 42 | 16 |
| 1 | 17 | 25 | 22 | 17 | 21 | 21 | 7 |
| 0 | 0 | 0 | 0 | 0 | 0 | 0 | 0 |

| Detection Probability by Probit Analysis[c] | Limit of Detection (LOD) in Copies/mL | | | | | | |
|---|---|---|---|---|---|---|---|
| 95% LOD | 12.7 | 13.0 | 13.7 | 14.6 | 10.2 | 18.9 | 69.6 |
| (95% fiducial limits) | (9.6-18.6) | (9.6-19.7) | (10.1-20.7) | (11-21.5) | (7.7-15.2) | (13.9-28.8) | (35.3-256.7) |
| 50% LOD | 2.8 | 2.4 | 2.5 | 2.9 | 2.2 | 2.9 | 9.0 |
| (95% fiducial limits) | (2.4-3.3) | (2.0-2.9) | (2.0-3.0) | (2.4-3.5) | (1.8-2.6) | (2.4-3.6) | (5.5-14.8) |

[a]Based on GenBank accession numbers NC001434 (1), M74506 (2), AB630970 (3a), AB630971 (3b), FJ956757 (3f), AB161717 (4c) and AB602441 (6)
[b]Putative HEV genotype
[c]Using SAS 9.2 PROBIT normal model Cross-Reactivity In silico BLAST analysis of the HEV-specific oligos did not show sequence matches to other blood borne pathogens except hepatitis C virus (HCV). The HEV oligo SEQ ID NO:64 showed 100% identity to part of the HCV envelope gene (positions 199-213 in GenBank accession number JQ063881). It is expected that this will not cause any false positivity issue because all the rest of the HEV-specific oligo sequences (whole or in part) are not found in the HCV genomic sequence. This is supported by testing of HCV-positive samples which showed non-reactivity in the HEV assay. Other bloodborne viruses (human immunodeficiency virus 1, hepatitis B virus, and West Nile virus) tested were also non-reactive for the HEV assay.

TABLE 18

HEV Cross-reactivity with Bloodborne Pathogens

| Condition | Blood Borne Viruses Added | Level | n | Mean S/CO* | % Reactivity |
|---|---|---|---|---|---|
| HEV Positive (30 IU/mL WHO IS added) | HIV-1 Type B (IIIB) | 100 c/mL | 8 | 23.57 | 100% |
| | HIV-1 Group O | 100 c/mL | 9 | 27.95 | 100% |
| | HCV 1A | 100 c/mL | 9 | 28.34 | 100% |
| | HCV 2B | ~300 c/mL | 9 | 28.32 | 100% |

TABLE 18-continued

HEV Cross-reactivity with Bloodborne Pathogens

| Condition | Blood Borne Viruses Added | Level | n | Mean S/CO* | % Reactivity |
|---|---|---|---|---|---|
| | HBV | ~32 IU/mL | 8 | 25.84 | 100% |
| | WNV Sample 022 | 3,000 c/mL | 9 | 28.74 | 100% |
| | WNV Sample 688 | 3,000 c/mL | 9 | 28.15 | 100% |
| | WNV Sample 630 | 3,000 c/mL | 9 | 22.64 | 100% |
| HEV | HIV-1 Type B (IIIB) | 100 c/mL | 9 | 0.01 | 0% |
| Negative | HIV-1 Group O | 100 c/mL | 9 | 0.02 | 0% |
| | HCV 1A | 100 c/mL | 9 | 0.02 | 0% |
| | HCV 2B | ~300 c/mL | 8 | 0.03 | 0% |
| | HBV | ~32 IU/mL | 9 | 0.02 | 0% |
| | WNV Sample 022 | 3,000 c/mL | 9 | 0.01 | 0% |
| | WNV Sample 688 | 3,000 c/mL | 9 | 0.03 | 0% |
| | WNV Sample 630 | 3,000 c/mL | 9 | 0.02 | 0% |

*S/CO (Signal to Cutoff) > or = 1.0 considered reactive

Specificity

The specificity of the HEV assay on was determined to be 99.95% (95% Score CI: 99.73%-99.99%) for 2,100 unlinked, frozen plasma specimens. The data showed excellent specificity of the HEV assay in frozen plasma specimens.

TABLE 19

HEV Specificity on Frozen Plasma Specimens

| | N | % |
|---|---|---|
| Specimens Tested | 2,100 | 100 |
| Valid Results | 2,100 | 100 |
| Initial Reactive | 1 | 0.05 |
| Repeat Reactive | 0 | 0 |
| Specificity (95% CI)* | 99.95% (99.73-99.99) | |

*CI = Confidence Interval using Score method

Probe Design

HEV probe oligo SEQ ID NO:71 showed an increased detection signal for HEV-3f relative to SEQ ID NO:55 [12,13], increasing the HEV 3f sensitivity from an 95% LOD of 12.4 c/mL to 10.2 c/mL and the RLU signal to a level more comparable to the other HEV genotypes tested.

Example 4

This example describes the determination of HEV RNA prevalence in blood donors and the performance characteristics of an HEV amplification and detection assay using oligonucleotides as described above.

Methods

Studies were conducted to show the analytical sensitivity to the HEV WHO International Standard (Paul Ehrlich Institute (PEI) code 6329/10) and RNA transcripts of all four clinically relevant HEV genotypes (1-4), and clinical specificity of the HEV assay described above ("the HEV assay"). Plasma (for nucleic acid testing) was collected from ~10,000 unlinked, volunteer whole blood donors. Samples were tested for HEV RNA using the HEV assay on the automated Panther system (Hologic, Inc., cat. no. 303095). Samples that were repeatedly reactive using TMA were confirmed by PCR and sequence analysis.

Results

The HEV assay showed a 95% limit of detection (LOD) of 7.9 IU/mL using the WHO Standard and 14.4 copies/mL using HEV 3a RNA transcript that had the same sequence as the HEV WHO Standard (see Tables 20 and 21). The assay detected all four HEV genotypes with a 95% LOD ranging from 7.9 to 17.7 copies/mL using RNA transcripts for HEV 1, 2, 3a, 3b, 3f and 4c (see Table 23). A total of 9,998 blood donations were screened for HEV RNA using the TMA assay. Three TMA repeat reactive donations were identified and confirmed positive by testing independent aliquots with PCR. One sample was determined to be genotype 3f by sequence analysis. Based on this study, HEV RNA prevalence rate in these blood donations was estimated to be 1 in 3,333 or 0.03% and the clinical specificity of the HEV assay was determined to be 99.99% (see Table 22 and Table 24).

TABLE 20

Analytical Sensitivity to HEV WHO International Standard (PEI) code 6329/10

| | % Reactivity (95% CI) | | | | | |
|---|---|---|---|---|---|---|
| | 90[†] | 30 | 10 | 3 | 1 | 0 |
| HEV WHO IU/mL (95% CI) | 100 (98-100) | 100 (98-100) | 98 (94-99) | 67 (60-74) | 27 (20-34) | 0 (0-5) |
| HEV3a IVT c/mL (95% CI) | 100 (95-100) | 100 (95-100) | 88 (71-93) | 38 (28-49) | 20 (14-31) | 0 (0-5) |

WHO, n = 162, In Vitro Transcript (IVT) & negative, n = 81
[†]The values 90, 30, 10, 3, 1 and 0 in the row above the percent reactivity results refer to IU/mL in the TMA reaction for the HEV WHO standard, and refer to copies/mL in the TMA reaction for the HEV3a IVT.

TABLE 21

Analytical Sensitivity to HEV WHO International Standard (PEI) code 6329/10

| Detection Probability | HEV WHO Std IU/mL (95% Fiducial Limits) | HEV3a IVT, c/mL (95% Fiducial Limits) |
|---|---|---|
| 95% | 7.89 (6.63-9.83) | 14.40 (11.28-20.14) |
| 50% | 2.02 (1.71-2.32) | 3.63 (2.92-4.37) |

TABLE 22

HEV RNA Prevalence Among Blood Donations

| n | HEV RNA Prevalence (Rate) |
|---|---|
| 9,998 | 3 or 1 in 3,333 (0.03%; 95% CI: 0.01%-0.09%) |

TABLE 23

Analytical Sensitivity to HEV Genotype 1-4 In Vitro Transcripts

| Copies/mL | Percent Reactivity of Genotype[1] IVTs | | | | | |
|---|---|---|---|---|---|---|
| (n = 81) | HEV1 | HEV2 | HEV3a | HEV3b | HEV3f | HEV4c |
| 90 | 100 | 100 | 100 | 100 | 100 | 100 |
| 30 | 100 | 100 | 100 | 100 | 100 | 100 |
| 10 | 96 | 95 | 88 | 86 | 98 | 80 |
| 3 | 77 | 42 | 38 | 46 | 59 | 36 |
| 1 | 31 | 27 | 20 | 12 | 20 | 19 |
| 0 | 0 | 0 | 0 | 0 | 0 | 0 |

| Detection Probability[2] | Limit of Detection in Copies/mL | | | | | |
|---|---|---|---|---|---|---|
| 95% LOD | 7.88 | 11.32 | 14.40 | 13.72 | 8.26 | 17.66 |
| (95% fiducial limits) | 6.11-11.26 | 8.83-16.03 | 11.28-20.14 | 10.89-18.78 | 6.65-11.11 | 13.77-24.74 |
| 50% LOD | 1.64 | 2.84 | 3.63 | 3.74 | 2.48 | 4.16 |
| (95% fiducial limits) | 1.21-2.06 | 2.26-3.44 | 2.92-4.37 | 3.03-4.47 | 2.01-2.96 | 3.34-5.03 |

[1]Based on GenBank accession numbers NC001434 (1), M74506 (2), AB630970 (3a), AB630971 (3b), FJ956757 (3f), AB161717 (4c)
[2]SAS Enterprise Guide 5.1 Probit Analysis using Gompertz model

TABLE 24

HEV Assay Specificity Testing Results of Blood Donations

| | n | % |
|---|---|---|
| #Unique Donations Tested | 9,998 | 100.00 |
| #Valid Nonreactive Retest Results | 9,995 | 99.97 |
| #Initial Reactives | 4 | 0.04 |
| #Repeat Reactives | 3 | 0.03 |
| Specificity Rate | 99.99% (95% CI: 99.94%-100.00%) | |

DISCUSSION/CONCLUSION

Results showed that the HEV assay was sensitive and specific, and detected all four clinically relevant HEV genotypes. Testing of nearly 10,000 individual blood donors for this study yielded three HEV RNA confirmed positive donations resulting in an HEV RNA prevalence rate of 0.03%. Based on the performance demonstrated in this study, the HEV assay may be useful for screening blood donations for HEV RNA.

SEQUENCES

TABLE 25

Exemplary Oligomer Sequences, Reference Sequences, and Regions

| SEQ ID NO: | Oligonucleotide Sequence | Oligonucleotide Description |
|---|---|---|
| 1 | Accession No. AB074918.2 GI:21218075 | HEV reference sequence |
| 2 | aagacauguuauucauuccaccc | Target-hybridizing sequence of SEQ ID NO: 2 |
| 3 | aagacauguuauucauuccacccTTTAAAAA | Target capture oligo |
| 4 | aagacauguuauucauucYWccc | Target-hybridizing sequence of target capture oligo |
| 5 | TgaTTgTcagcccTTcgC | Probe |
| 6 | aagacauguuauucauucuaccc | Target-hybridizing sequence of SEQ ID NO: 7 |
| 7 | aagacauguuauucauucuacccTTTAAAAA | Target capture oligo |
| 8 | aagacauguuauucauucYWcccTTTAAAAA | Target capture oligo |
| 9 | AATTTAATACGACTCACTATAGGGAGAAGGG GTTGGTTGGATGAATATAG | T7 amp oligo |
| 10 | AATTTAATACGACTCACTATAGGGAGAAGGG GTTGGTTGGATGAATATAGG | T7 amp oligo |
| 11 | AATTTAATACGACTCACTATAGGGAGAAGGG GTTGGTTGGATGAATATAGGG | T7 amp oligo |

TABLE 25-continued

Exemplary Oligomer Sequences, Reference Sequences, and Regions

| SEQ ID NO: | Oligonucleotide Sequence | Oligonucleotide Description |
| --- | --- | --- |
| 12 | AATTTAATACGACTCACTATAGGGAGAAGGGGTTGGTTGGATGAATATAGGGGA | T7 amp oligo |
| 13 | ctatgctgcccgcgccaccg | Amp oligo hybridizing region |
| 14 | AATTTAATACGACTCACTATAGGGAGAGGCGAAGGGGTTGGTTGGATGAA | T7 amp oligo |
| 15 | AATTTAATACGACTCACTATAGGGAGAGGGCGAAGGGGTTGGTTGGATGAA | T7 amp oligo |
| 16 | ccggcggtgtttctggggtgac | Amp oligo hybridizing region |
| 17 | AATTTAATACGACTCACTATAGGGAGAGGTTGGTTGGATGAATATAG | T7 amp oligo |
| 18 | AATTTAATACGACTCACTATAGGGAGAGGTTGGTTGGATGAATATAGG | T7 amp oligo |
| 19 | AATTTAATACGACTCACTATAGGGAGAGGTTGGTTGGATGAATATAGGG | T7 amp oligo |
| 20 | AATTTAATACGACTCACTATAGGGAGAGGTTGGTTGGATGAATATAGGGGA | T7 amp oligo |
| 21 | AGGGGTTGGTTGGATGAATATAG | Target-hybridizing sequence of SEQ ID NO: 9 |
| 22 | AGGGGTTGGTTGGATGAATATAGG | Target-hybridizing sequence of SEQ ID NO: 10 |
| 23 | AGGGGTTGGTTGGATGAATATAGGG | Target-hybridizing sequence of SEQ ID NO: 11 |
| 24 | AGGGGTTGGTTGGATGAATATAGGGGA | Target-hybridizing sequence of SEQ ID NO: 12 |
| 25 | GGTTGGTTGGATGAA | Amp oligo core sequence |
| 26 | tgctgcccgcgcc | Amp oligo core sequence |
| 27 | CGGCGGTGGTTTCT | Amp oligo core sequence |
| 28[1] | NCGGCGGTGGTTTCTNN | Non-T7 amp oligo |
| 29 | CCGGCGGTGGTTTCT | Non-T7 amp oligo |
| 30 | CCGGCGGTGGTTTCTG | Non-T7 amp oligo |
| 31 | CCGGCGGTGGTTTCTGG | Non-T7 amp oligo |
| 32 | CGGCGGTGGTTTCTGG | Non-T7 amp oligo |
| 33 | CTATGCTGCCCGCGCC | Non-T7 amp oligo |
| 34 | CTATGCTGCCCGCGCCA | Non-T7 amp oligo |
| 35 | CTATGCTGCCCGCGCCAC | Non-T7 amp oligo |
| 36 | GAAGGGCTGAGAATCA | Probe protection oligo |
| 37 | gaccggguugauucuC | Probe |
| 38 | gaccggguugauucu | Probe |
| 39 | gacagggttgattctcagcccttcgccc | Probe target region |
| 40 | GAGAATCAACCCGGT | Probe protection oligo |
| 41 | gaccgggTTgaTTcTC | Probe |
| 42 | gaggggcgcugggacuggucg | Target-hybridizing sequence of SEQ ID NO: 43 |

TABLE 25-continued

Exemplary Oligomer Sequences,
Reference Sequences, and Regions

| SEQ ID NO: | Oligonucleotide Sequence | Oligonucleotide Description |
|---|---|---|
| 43 | gagggcgcugggacuggucgTTTAAAAAAA AAAAAAAAAAAAAAAAAAAAAAA | Target capture oligo |
| 44 | tgcctatgctgcccgcgccaccggccggtca gccgtctggccgtcgccgtgggcggcgcagc ggcggtgccggcggtggtttctggggtgac | Amp oligo hybridizing region |
| 45 | GGCGAAGGGGTTGGTTGGATGAA | Target-hybridizing sequence of SEQ ID NO: 14 |
| 46 | GGGCGAAGGGGTTGGTTGGATGAA | Target-hybridizing sequence of SEQ ID NO: 15 |
| 47 | SGGCGAAGGGGTTGGTTGGATGAATATAGGG GA | Amp oligo hybridizing region |
| 48 | GGTTGGTTGGATGAATATAG | Target-hybridizing sequence of SEQ ID NO: 17 |
| 49 | GGTTGGTTGGATGAATATAGG | Target-hybridizing sequence of SEQ ID NO: 18 |
| 50 | GGTTGGTTGGATGAATATAGGG | Target-hybridizing sequence of SEQ ID NO: 19 |
| 51 | GGTTGGTTGGATGAATATAGGGA | Target-hybridizing sequence of SEQ ID NO: 20 |
| 52 | GGTTTCTGGGGTGAC | Non-T7 amp oligo |
| 53 | GTGGTTTCTGGGGTGA | Non-T7 amp oligo |
| 54 | GTGGTTTCTGGGGTGAC | Non-T7 amp oligo |
| 55 | GUUGAUUCUCAGCCCUUCGCCC | Probe |
| 56 | SGGCGAAGGGGTTGGTTGGATGAA | Target-hybridizing sequence of SEQ ID NO: 57 |
| 57 | AATTTAATACGACTCACTATAGGGAGAsGGC GAAGGGGTTGGTTGGATGAA | T7 amp oligo |
| 58 | acagggttgattctcagcccttcgccctccc ctatattcatccaaccaacccttcgccs | Partial amplicon |
| 59 | ccggcggtggtttctggggtgacagggttga ttctcagcccttcgccc | Partial amplicon |
| 60 | tatgctgcccgcgccaccggccggtcagccg tctggccgtcgccgtgggcggcgcagcggcg gtgccggcggtggtttctggggtgacagggt tgattct | Partial amplicon |
| 61 | TGCCTATGCTGCCCGCGCCAC | Non-T7 amp oligo |
| 62 | TGCTGCCCGCGCCA | Non-T7 amp oligo |
| 63 | tgcctatgctgcccgcgccaccg | Amp oligo hybridizing region |
| 64 | TGCTGCCCGCGCCAC | Non-T7 amp oligo |
| 65 | TGCTGCCCGCGCCACC | Non-T7 amp oligo |
| 66 | TGCTGCCCGCGCCACCG | Non-T7 amp oligo |
| 67 | ugauucucagcccuucgC | Probe |
| 68 | agggttgattctcagcccttcgccc | Probe target region |
| 69 | gccggtcagccgtctggccgtcgccgtgggc ggcgcagcggcggtgccggcggtggtttctg gggtgacagggttgattctcagcccttcgcc c | Probe target region |

TABLE 25-continued

Exemplary Oligomer Sequences,
Reference Sequences, and Regions

| SEQ ID NO: | Oligonucleotide Sequence | Oligonucleotide Description |
|---|---|---|
| 70 | tgcctatgctgcccgcgccaccggccggtca gccgtctggccgtcgccgtgggcggcgcagc ggcggtgccggcggtggtttctggggtgaca gggttgattctcagcccttcgccctcccta tattcatccaaccaacccttcgccg | Amplicon |
| 71 | ugauugucagcccuucgC | Probe |
| 72 | ugauugucagcccuucg | Probe |
| 73 | AATTTAATACGACTCACTATAGGGAGA | T7 promoter sequence |
| 74 | accgccgcugcgccgcccacggcgTTTAAAA | Target capture oligo |
| 75 | accgccgcugcgccgcccacggcg | Target-hybridizing sequence of SEQ ID NO: 74 |
| 76 | agcggcggggcgcugggccuggucTTTAAAA | Target capture oligo |
| 77 | agcggcggggcgcugggccugguc | Target-hybridizing sequence of SEQ ID NO: 76 |
| 78 | ccacaagcuuagaagauagagagG | Internal control probe |
| 79 | CTATCTTCTAAGCTTG | Probe protection oligo |

Note that the amplicon and partial amplicon sequences are illustrated herein and in the Sequence Listing as DNA, however, ordinarily skilled artisans understand that amplification products generated during TMA reactions are either RNA or DNA, depending upon the stage in the amplification cycle. DNA designation is provided herein only for convenience, and not limitation.
[1]N at position 1 is C or is absent, N at position 16 is G or is absent, and N at position 17 is G or is absent. In some embodiments, if N at position 16 is G and N at position 17 is absent, then N at position 1 is C.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A combination of at least two oligomers for determining the presence or absence of hepatitis E virus (HEV) in a sample, said oligomer combination comprising:
   at least two amplification oligomers for amplifying a target region of an HEV target nucleic acid, wherein
   (a) at least one amplification oligomer is selected from the group consisting of
      (i) an oligomer comprising a target-hybridizing sequence consisting of a sequence that is from about 14 to about 23 contiguous nucleotides contained in the sequence of SEQ ID NO:63 and that includes at least the sequence of SEQ ID NO:26, including RNA equivalents and DNA/RNA chimerics thereof, and
      (ii) an oligomer comprising a target-hybridizing sequence consisting of SEQ ID NO:28, including RNA equivalents and DNA/RNA chimerics thereof; and
   (b) at least one amplification oligomer that is a promoter primer comprising a target-hybridizing sequence consisting of SEQ ID NO:24 or SEQ ID NO:56, including RNA equivalents and DNA/RNA chimerics thereof and further comprising a promoter sequence joined to the 5' end of the target hybridizing sequence.

2. A kit comprising a combination of at least two oligomers for determining the presence or absence of hepatitis E virus (HEV) in a sample, said oligomer combination comprising:
   at least two amplification oligomers for amplifying a target region of an HEV target nucleic acid, wherein
   (a) at least one amplification oligomer is selected from the group consisting of
      (i) an oligomer comprising a target-hybridizing sequence consisting of a sequence that is from about 14 to about 23 contiguous nucleotides contained in the sequence of SEQ ID NO:63 and that includes at least the sequence of SEQ ID NO:26, including RNA equivalents and DNA/RNA chimerics thereof, and
      (ii) an oligomer comprising a target-hybridizing sequence consisting of SEQ ID NO:28, including RNA equivalents and DNA/RNA chimerics thereof; and
   (b) at least one amplification oligomer that is a promoter primer comprising a target-hybridizing sequence consisting of SEQ ID NO:24 or SEQ ID NO:56, including RNA equivalents and DNA/RNA chimerics thereof and further comprising a promoter sequence joined to the 5' end of the target hybridizing sequence.

3. A reaction mixture comprising a combination of at least two oligomers for determining the presence or absence of hepatitis E virus (HEV) in a sample, said oligomer combination comprising:
   at least two amplification oligomers for amplifying a target region of an HEV target nucleic acid, wherein
   (a) at least one amplification oligomer is selected from the group consisting of
      (i) an oligomer comprising a target-hybridizing sequence consisting of a sequence that is from about 14 to about 23 contiguous nucleotides contained in the sequence of SEQ ID NO:63 and that includes at least the sequence of SEQ ID NO:26, including RNA equivalents and DNA/RNA chimerics thereof, and (ii) an oligomer comprising a target-hybridizing sequence consisting of SEQ ID NO:28, including RNA equivalents and DNA/RNA chimerics thereof; and (b) at least one amplification oligomer that is a promoter primer comprising a target-hybridizing sequence consisting of SEQ ID NO:24 or SEQ ID NO:56, including RNA equivalents and DNA/RNA chimerics thereof and further comprising a promoter sequence joined to the 5' end of the target hybridizing sequence.

4. The reaction mixture of claim 3, wherein the at least one amplification oligomer of (a) comprises a target-hybridizing sequence consisting of SEQ ID NO:29, SEQ ID NO:30, SEQ ID NO:31, SEQ ID NO:32, SEQ ID NO:61, SEQ ID NO:62, SEQ ID NO:64, SEQ ID NO:65, or SEQ ID NO:66, including RNA equivalents and DNA/RNA chimerics thereof.

5. The reaction mixture of claim 3, wherein the at least one amplification oligomer of (a) comprises a target-hybridizing sequence consisting of SEQ ID NO:29 or SEQ ID NO:64, including RNA equivalents and DNA/RNA chimerics thereof.

6. The reaction mixture of claim 3, wherein the at least one amplification oligomer of (a) comprises the target-hybridizing sequence consisting of SEQ ID NO:28, including RNA equivalents and DNA/RNA chimerics thereof.

7. The reaction mixture of claim 6, wherein the at least one amplification oligomer of (a) comprises a target-hybridizing sequence consisting of SEQ ID NO:29, SEQ ID NO:30, SEQ ID NO:31, or SEQ ID NO:32, including RNA equivalents and DNA/RNA chimerics thereof.

8. The reaction mixture of claim 3, wherein the at least one amplification oligomer of (b) comprises a target-hybridizing sequence consisting of SEQ ID NO:24 or SEQ ID NO:46, including RNA equivalents and DNA/RNA chimerics thereof.

9. The reaction mixture of claim 3, wherein the at least one amplification oligomer of (b) comprises a target-hybridizing sequence consisting of SEQ ID NO:56, including RNA equivalents and DNA/RNA chimerics thereof.

10. The reaction mixture of claim 9, wherein the nucleobase at position 1 of SEQ ID NO:56 is guanine (G).

11. The reaction mixture of claim 3, wherein said combination comprises an amplification oligomer as in (a)(i), an amplification oligomer as in (a)(ii), a first amplification oligomer as in (b), and a second amplification oligomer as in (b).

12. The reaction mixture of claim 11, wherein
the amplification oligomer as in (a)(i) comprises the target-hybridizing sequence consisting of SEQ ID NO: 65, or an RNA equivalent or DNA/RNA chimeric thereof;
the amplification oligomer as in (a)(ii) comprises the target-hybridizing sequence consisting of SEQ ID NO: 29, or an RNA equivalent or DNA/RNA chimeric thereof;
the first amplification oligomer as in (b) comprises the target-hybridizing sequence consisting of SEQ ID NO:24, or an RNA equivalent or DNA/RNA chimeric thereof; and
the second amplification oligomer as in (b) comprises the target-hybridizing sequence consisting of SEQ ID NO:56, or an RNA equivalent or DNA/RNA chimeric thereof.

13. The reaction mixture of claim 3, wherein said combination comprises a first amplification oligomer as in (a)(ii), a second amplification oligomer as in (a)(ii), a first amplification oligomer as in (b), and a second amplification oligomer as in (b).

14. The reaction mixture of claim 3, wherein the combination comprises a set of first, second, and third amplification oligomers comprising a set of first, second, and third target-hybridizing sequences, respectively, wherein the set of target-hybridizing sequences consists of:

(i) SEQ ID NO:65, SEQ ID NO:29, and SEQ ID NO:24, including RNA equivalents and DNA/RNA chimerics thereof;

(ii) SEQ ID NO:65, SEQ ID NO:29, and SEQ ID NO:56, including RNA equivalents and DNA/RNA chimerics thereof;

(iii) SEQ ID NO:29, SEQ ID NO:24, and SEQ ID NO:56, including RNA equivalents and DNA/RNA chimerics thereof;

(iv) SEQ ID NO:66, SEQ ID NO:24, and SEQ ID NO:56, including RNA equivalents and DNA/RNA chimerics thereof;

(v) SEQ ID NO:65, SEQ ID NO:24, and SEQ ID NO:56, including RNA equivalents and DNA/RNA chimerics thereof; [randl] or (vi) SEQ ID NO:62, SEQ ID NO:29, and SEQ ID NO:56, including RNA equivalents and DNA/RNA chimerics thereof.

15. The reaction mixture of claim 3, wherein the at least one amplification oligomer of (a) comprises a target-hybridizing sequence consisting of SEQ ID NO:31, SEQ ID NO:30, SEQ ID NO:29, SEQ ID NO:66, SEQ ID NO:65, SEQ ID NO:64, SEQ ID NO:62, SEQ ID NO:35, SEQ ID NO:34, SEQ ID NO:33, or SEQ ID NO:61, including RNA equivalents and DNA/RNA chimerics thereof.

16. The reaction mixture of claim 3, wherein the promoter sequence is a T7 promoter sequence.

17. The reaction mixture of claim 16, wherein the T7 promoter sequence has the sequence shown in SEQ ID NO:73.

18. The reaction mixture of claim 3, further comprising at least one detectably labeled detection probe oligomer comprising a target-hybridizing sequence that is from about 14 to about 28 nucleotides in length and is configured to specifically hybridize to a target sequence contained within SEQ ID NO:39 or the complement thereof, and wherein the at least one detection probe oligomer contains a 2'-methoxy backbone at one or more linkages in the nucleic acid backbone.

19. The reaction mixture of claim 3, wherein at least one of the amplification oligomers of (a) and (b) contains a 2'-methoxy backbone at one or more linkages in the nucleic acid backbone.

* * * * *

SEQUENCE LISTING

```
<160> NUMBER OF SEQ ID NOS: 79

<210> SEQ ID NO 1
<211> LENGTH: 7256
<212> TYPE: DNA
<213> ORGANISM: Hepatitis E virus
<300> PUBLICATION INFORMATION:
<308> DATABASE ACCESSION NUMBER: AB074918.2 GI:21218075
<309> DATABASE ENTRY DATE: 2008-12-17
<313> RELEVANT RESIDUES IN SEQ ID NO: (1)..(7256)

<400> SEQUENCE: 1
gcagaccacg tatgtggtcg atgccatgga ggcccatcag ttcattaagg ctcctggcat      60
tactactgcc attgagcagg ctgctctggc tgcggccaat tccgccttgg cgaatgctgt     120
ggtggtccgg ccgttcttat ctcgtgtaca aactgagatt cttattaatt tgatgcaacc     180
ccggcagttg gttttccgcc ctgaggtgct ctggaatcac cctatccagc gggttataca     240
taatgaattg gaacagtact gccgggcccg ggccggccgt tgcctggagg ttgggctca     300 cccgaggtcc attaatgaca atcccaatgt cctgcacagg tgctttctta gaccggttgg     360
ccgagacgtc cagcgctggt actctgcccc caccgtggc cctgcggcca actgcgccg     420 ctccgcgttg cgtggtctcc ctcccgctga ccgcacttat tgctttgatg gattctcccg     480
```

-continued

```
ctgtgctttt gctgcagaga ccggcgtggc cctttactct ctgcatgacc tttggccagc      540
tgatgtcgca gaggctatgg cccgccacgg gatgacacgc ctatatgctg cactacacct      600
ccctcctgag gtgctgttgc cacccggcac ttaccacaca acctcgtatc tcctgatcca      660
cgacggcgac cgtgccgtcg taacttatga gggcgatact agtgcaggct acaatcacga      720
tgtttccata cttcgtgcgt ggatccgtac tactaaaata gttggtgacc acccgttggt      780
tatagagcgt gtgcgggcca ttggatgtca ttttgtgctg ctgctcaccg cagcccctga      840
gccgtcacct atgccttatg tccccctaccc tcgttcaact gaggtgtatg tacgatctat      900
atttggccct ggtggctccc catctttgtt cccgtcagcc tgctctacta aatctacttt      960
tcatgctgtc ccggttcata tctgggaccg gcttatgctt tttggtgcca ccctggacga     1020
tcaggcgttt tgttgttcac ggctcatgac ttacctccgt ggtattagct acaaggtcac     1080
tgtcggtgcg cttgttgcta atgagggatg gaatgcctct gaggacgccc ttactgcagt     1140
gatcactgcg gcttacctga ctatttgcca ccaacgctac cttcgaaccc aggcgatatc     1200
caagggtatg cgccggttgg aggttgagca tgcccagaaa ttcatcacaa ggctctacag     1260
ctggctattt gagaaatctg gtcgtgatta tatccccggc cgccagcttc agttctatgc     1320
acaatgtcgg cggtggttat ctgcaggctt ccacctcgac cccagggtgc ttgtcttcga     1380
tgaagcagtg ccatgccgct gtaggacgtt tttgaagaag gtcgcgggta aattctgctg     1440
ttttatgcgg tggctagggc aggagtgcac ctgtttcttg gagccagctg agggcctaat     1500
tggagaccaa ggccatgata atgaggccta tgagggttct gaggtcgacc cggctgaacc     1560
tgcacatctt gatgtttcgg ggacctatgc tgtccatggg catcagcttg aggcccttta     1620
tagggcactc aatgtcccac atgatattgc cgctcgagcc tcccggctaa cggctactgt     1680
cgagcttgtt gcaagtccag accgcttaga gtgccgtact gtgcttggta ataagacctt     1740
tcggacaacg gtggttgatg gtgcccatct tgaagcaaat ggccctgagg agtatgttct     1800
atcattcgac gcctctcgtc agtctatggg ggccggatcg cacagcctca catatgagct     1860 caccectgct ggtctgcagg tcaggatttc atctaatggc ttggattgta ccgccgtatt     1920
ccctcccggc ggcgccccta cgccgcacc gggggaggtg gcagccttct gcagcgccct     1980
ttatagatat aacaggttca cccaacggca ctcgctaacc ggtggattat ggttacaccc     2040 tgagggggttg ctgggcatct tcccccecttt ctctcctgga cacatctggg agtctgctaa     2100 cccatttttgt ggggagggga ccttgtatac ccgaacctgg tcaacatctg gcttctctag     2160
cgacttctcc cccctgagg cggccgcccc tgttccggct gctgccccgg gctgccccca     2220 ccccaccccca cctgttagtg acatttgggt gctgccacca ccctcagagg agtcccagat     2280
cgatgcggca cctgtgcccc ctgtccctaa gactgttgga ttgcctagcc ccattgtact     2340
tgctcctccc tcccctcttc cttccccegt gcgtaagcca ccatcacccc cgccttctcg     2400
cactcgtcgt ctcctctaca cctatcctga cggcgctagg gtatatgcgg ggtcgttgtt     2460
tgaatcagac tgtgactggc tagttaacgc ctcaaatccg ggccaccgtc ctggaggtgg     2520
cctctgccac gccttttacc aacgcttccc agaggcgttt tacccaactg aattcattat     2580
gcgtgagggc cttgcagcat ataccctgac cccgcgccct atcattcatg cagtggctcc     2640
cgactatagg gtcgagcaga atccgaagag gcttgaggca gcgtaccggg aaacttgctc     2700
ccgtcgcggc accgctgcct atccgctttt gggctcgggt atataccagg tccctgttag     2760
tctcagtttt gatgcctggg aacgcaatca tcgcccggc gacgagcttt acttgactga     2820
gcccgctgca gcttggtttg aggctaataa gccatcgcag ccggcgctta ctataactga     2880
```

```
ggacacggct cgtacggcca atctggcatt agagattgat gccgccacag aggttggccg    2940
tgcttgtgcc ggctgcacta tcagcccggg ggttgtgcat taccagttta ctgccggggt    3000
cccgggctcg ggcaagtcaa ggtccataca acagggagac gtcgatgtgg tggttgtgcc    3060
cacccgggag cttcgtaata gttggcgccg ccggggtttt gcggctttca cacctcacac    3120
agcggcccgt gttactattg gtcgccgcgt tgtgattgat gaggctccgt ccctcccgcc    3180
gcacttgctg ctgctacaca tgcaacgggc ctcctcggtc catctcctcg gcgacccaaa    3240
tcagattcct gctattgatt ttgaacatgc cggcctggtc cccgcgatcc gtcccgagct    3300
tgcaccaacg agctggtggc atgttacaca ccgctgcccg gcagatgtgt gtgagcttat    3360
acgtggggcc taccctaaga tccagaccac gagtcgtgtg ctacggtccc tgttttggaa    3420
cgaaccggcc attggccaga agctggtttt cacgcaggct gctaaggctg ctaatcctgg    3480
tgcgatcacg gttcatgagg ctcagggtgc caccttcacg gagaccacaa tcatagccac    3540
ggctgatgct aggggcctta ttcagtcatc ccgagctcac gctatagtcg cactcacccg    3600
ccacactgag aagtgtgtta ttttagatgc ccccggccta ctgcgcgagg tcggtatttc    3660
agatgtgatt gtcaataact ttttccttgc tggtggagag gttggccacc accgcccctc    3720
cgtgatacct cgcggtaacc ccgatcagaa tctcgggact ctacaggcat tcccgccgtc    3780
ttgccagatt agtgcctacc accagttggc tgaggaatta ggccaccgcc agctcctgt    3840 cgccgccgtc ttacccccctt gcccggagct tgagcagggc ctgctctaca tgccacaaga    3900
gcttactgtg tccgatagtg tgttggtatt tgaactcaca gatatagtcc attgccgtat    3960
ggccgctcca agccagcgaa aggctgttct ctcaacactt gtcgggaggt atggccgtag    4020
aacgaaatta tatgaggcgg cacattcaga tgttcgtgag tccctagcta ggttcatccc    4080
cactatcggg cctgttcagg ccaccacatg tgagttgtat gagttggttg aggccatggt    4140
ggagaagggt caggacggct ctgccgtcct agagcttgac cttttgcaatc gtgacgtctc    4200 gcgtatcaca ttttttccaaa aggattgcaa taaattcaca actggtgaga ctattgccca    4260
tggcaaggtt ggccagggta tatcggcctg gagtaagacc ttctgtgccc tgtttggccc    4320
gtggttccgc gctatagaaa aagagatatt ggccctgctc ccgcctaata tcttttatgg    4380
cgacgcttat gaagagtcag tgtttgctgc cgctgtgtct ggggcggggt catgtatggt    4440
atttgaaaat gattttttcgg aatttgacag tactcagaac aacttctctc tcggccttga    4500
gtgtgtggtc atggaggagt gcggcatgcc ccagtggttg attaggttgt accatctggt    4560
tcggtcagcc tggatttttgc aggcgccgaa ggagtctctt aagggttttt ggaagaagca    4620
ctctggtgag cctggtaccc ttctctggaa caccgtctgg aacatggcga ttatagcgca    4680
ctgttacgag ttccgtgact ttcgcgttgc cgccttcaag ggtgatgatt cggtggtcct    4740
ttgcagcgac tatcggcaga gccgcaatgc ggctgcctta attgcaggct gtgggctcaa    4800
attgaaggtc gattatcgtc ctattgggct gtatgctggg gtggtggtgg ccctggttt    4860 ggggacactg cccgacgtgg tgcgttttgc tggtcggttg tctgaaaaga attggggccc    4920
cggccctgaa cgtgctgagc agctgcgtct cgctgtttgt gatttccttc gagggttgac    4980
gaatgttgcg caggtttgtg ttgatgttgt gtcccgtgtt tacggagtca gccccggct    5040 ggtacataac cttattggca tgctgcagac cattgccgat ggcaaggctc acttcacaga    5100
gaccattaaa cctgtgcttg accttacgaa ttccatcata cagcgggaag aatgaataac    5160
atgtcttttg catcgcccat gggatcacca tgcgccctag ggctgttctg ttgttgttcc    5220
```

```
tcgtgctttt gcctatgctg cccgcgccac cggccggtca gccgtctggc cgtcgccgtg    5280
ggcggcgcag cggcggtgcc ggcggtggtt tctggggtga cagggttgat tctcagccct    5340
tcgccctccc ctatattcat ccaaccaacc ccttcgccgc cgatgtcgtt tcacaacccg    5400
gggctggaac tcgccctcga cagccgcccc gccccttgg ctccgcttgg cgtgaccagt     5460
cccagcgccc ctccgctgcc cccgccgtc gatctgcccc agctggggct cgccgttga     5520 ccgctgtatc accggctcct gacacagccc ctgtgcctga tgttgattca cgcggtgcta    5580
tcctgcgccg gcagtacaat ctgtccacgt ccccgctcac gtcatctgtc gcctcgggca    5640
caaatctggt tctctatgct gccccgctta atcctctcct gccccttcag gatggcacca    5700
acactcatat tatggccact gaggcatcca attatgccca gtatcgggtt gttcgagcta    5760
cgatccgtta tcgcccgttg gtgccgaatg cagttggcgg ttatgctatt tctatttctt    5820
tttggcctca aaccacaact actcccacct ctgtcgacat gaattctatc acttccactg    5880
atgttaggat tttggttcag cccggcattg cctccgagtt agtcatccct agtgagcgcc    5940
tccactaccg caatcaaggc tggcgctctg ttgagaccac gggtgtggcc gaggaggagg    6000
ctacttccgg tctggtaatg ctttgtattc atggctctcc tgttaattcc tacactaata    6060
caccttatac tggtgcactg gggctccttg attttgcatt agagcttgaa tttagaaatc    6120
tgacacccgg gaacacaaac acccgtgttt cccggtatac cagcacagcc cgtcaccggc    6180
tgcgccgcgg tgctgatggg actgctgagc ttaccaccac agcagccaca cgtttcatga    6240
aggatttaca ttttactggc acgaatggtg ttggtgaggt gggtcgtggc atcgctctga    6300
cattgtttaa tctcgctgac acgcttctcg gtggtttacc gacagaattg atttcgtcgg    6360 ccggggtca actgtttta tcccgccctg ttgtctcggc caatggcgag ccaacagtaa       6420
agttatacac atctgttgag aatgcgcagc aagataaggg cattaccatc ccacacgata    6480
tagatctggg tgactcccgt gtggttattc aggattatga taaccagcac gagcaagatc    6540
ggcctactcc gtcacctgcc ccctcccgcc ctttctcagt tcttcgtgct aatgatgttc    6600
tgtggctctc cctcaccgcc gctgagtatg accagactac gtatgggtcg tccaccaacc    6660
ctatgtatgt ctccgacaca gtcacgctcg ttaatgtggc cactggagcc caggctgtgg    6720
cccgctctct tgattggtct aaagttacct tggatggccg ccccttact accattcagc    6780 agtattctaa gacattctat gtccttccgc tccgcgggaa gctgtctttc tgggaggctg    6840
gtacgactaa ggccggttac ccgtataatt ataatactac tgctagtgat cagatcttga    6900
ttgagaacgc ggccggccac cgtgtcgcta tttctaccta tactactagc ttgggtgccg    6960
gccctacctc gatctctgcg gtcggtgtac tagctccaca ttcggccctc gccgttctag    7020
aggacaccgt tgattacccc gcccgcgctc acacttttga tgatttctgc ccggagtgcc    7080
gtaccctcgg tttgcagggt tgtgcattcc agtctactat cgctgagctt cagcgtctta    7140
aaatgaaggt aggtaaaacc cgggagtctt aattaattcc ttttgtgccc ccttcgcagc    7200
tttctctggc tttatttctt atttctgctt ttcgcgctcc ctggaaaaaa aaaaaa        7256
```

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2
aagacauguu auucauucca ccc                                              23

<210> SEQ ID NO 3
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 3
aagacauguu auucauucca ccctttaaaa aaaaaaaaaa aaaaaaaaaa aaaaaa    56

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 4
aagacauguu auucauucyw ccc                                        23

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 5
tgattgtcag cccttcgc                                              18

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
aagacauguu auucauucua ccc                                        23

<210> SEQ ID NO 7
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 7
aagacauguu auucauucua ccctttaaaa aaaaaaaaaa aaaaaaaaaa aaaaaa    56

<210> SEQ ID NO 8
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 8
aagacauguu auucauucyw ccctttaaaa aaaaaaaaaa aaaaaaaaaa aaaaaa    56

<210> SEQ ID NO 9
<211> LENGTH: 50
<212> TYPE: DNA
<213> ORGANISM: Artificial Sequence
<220> FEATURE:

```
<223> OTHER INFORMATION: Synthetic Oligonucleotide
<220> FEATURE:
<221> NAME/KEY: promoter
<222> LOCATION: (1)..(27)

<400> SEQUENCE: 9
aatttaatac gactcactat agggagaagg ggttggttgg atgaatatag              50

<210> SEQ ID NO 10
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 10
aatttaatac gactcactat agggagaagg ggttggttgg atgaatatag g            51

<210> SEQ ID NO 11
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 11
aatttaatac gactcactat agggagaagg ggttggttgg atgaatatag gg           52

<210> SEQ ID NO 12
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 12
aatttaatac gactcactat agggagaagg ggttggttgg atgaatatag ggga         54

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ctatgctgcc cgcgccaccg                                               20

<210> SEQ ID NO 14
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 14
```

```
aatttaatac gactcactat agggagaggc gaaggggttg gttggatgaa        50
```

<210> SEQ ID NO 15
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 15

```
aatttaatac gactcactat agggagaggg cgaaggggtt ggttggatga a      51
```

<210> SEQ ID NO 16
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 16

```
ccggcggtgg tttctggggt gac                                     23
```

<210> SEQ ID NO 17
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 17

```
aatttaatac gactcactat agggagaggt tggttggatg aatatag           47
```

<210> SEQ ID NO 18
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 18

```
aatttaatac gactcactat agggagaggt tggttggatg aatatagg          48
```

<210> SEQ ID NO 19
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 19

```
aatttaatac gactcactat agggagaggt tggttggatg aatataggg         49
```

<210> SEQ ID NO 20
<211> LENGTH: 51
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 20
aatttaatac gactcactat agggagaggt tggttggatg aatatagggg a        51

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 21
aggggttggt tggatgaata tag                                       23

<210> SEQ ID NO 22
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 22
aggggttggt tggatgaata tagg                                      24

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 23
aggggttggt tggatgaata taggg                                     25

<210> SEQ ID NO 24
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 24
aggggttggt tggatgaata taggga                                    27

<210> SEQ ID NO 25
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 25
ggttggttgg atgaa                                                15

<210> SEQ ID NO 26
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 26
```

-continued tgctgcccgc gcc                                                              13

<210> SEQ ID NO 27
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 27
cggcggtggt ttct                                                             14

<210> SEQ ID NO 28
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: N is c or the residue is absent from the
      sequence.
<220> FEATURE:
<221> NAME/KEY: misc_feature
<222> LOCATION: (16)..(16)
<223> OTHER INFORMATION: N is g or the residue is absent from the
      sequence.
<220> FEATURE:
<221> NAME/KEY: misc_feature
<222> LOCATION: (17)..(17)
<223> OTHER INFORMATION: N is g or the residue is absent from the
      sequence.

<400> SEQUENCE: 28
ncggcggtgg tttctnn                                                          17

<210> SEQ ID NO 29
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 29
ccggcggtgg tttct                                                            15

<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 30
ccggcggtgg tttctg                                                           16

<210> SEQ ID NO 31
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 31
ccggcggtgg tttctgg                                                          17

```
<210> SEQ ID NO 32
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 32
cggcggtggt ttctgg                                                    16

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 33
ctatgctgcc cgcgcc                                                    16

<210> SEQ ID NO 34
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 34
ctatgctgcc cgcgcca                                                   17

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
ctatgctgcc cgcgccac                                                  18

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 36
gaagggctga gaatca                                                    16

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37
gaccggguug auucuc                                                    16

<210> SEQ ID NO 38
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 38
gaccggguug auucu                                               15

<210> SEQ ID NO 39
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 39
gacagggttg attctcagcc cttcgccc                                 28

<210> SEQ ID NO 40
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 40
gagaatcaac ccggt                                               15

<210> SEQ ID NO 41
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 41
gaccgggttg attctc                                              16

<210> SEQ ID NO 42
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 42
gaggggcgcu gggacugguc g                                        21

<210> SEQ ID NO 43
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 43
gaggggcgcu gggacugguc gtttaaaaaa aaaaaaaaaa aaaaaaaaaa aaaa    54

<210> SEQ ID NO 44
<211> LENGTH: 92
<212> TYPE: DNA
<213> ORGANISM: Artificial Sequence
<220> FEATURE:
<223> OTHER INFORMATION: Synthetic Oligonucleotide

<400> SEQUENCE: 44
tgcctatgct gcccgcgcca ccggccggtc agccgtctgg ccgtcgccgt gggcggcgca    60
gcggcggtgc cggcggtggt ttctggggtg ac                                92
```

```
<210> SEQ ID NO 45
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 45 ggcgaaggggg ttggttggat gaa                                          23

<210> SEQ ID NO 46
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
gggcgaaggg gttggttgga tgaa                                          24

<210> SEQ ID NO 47
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 47
sggcgaaggg gttggttgga tgaatatagg gga                                33

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
ggttggttgg atgaatatag                                               20

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 49
ggttggttgg atgaatatag g                                             21

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 50
ggttggttgg atgaatatag gg                                            22

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide
```

```
<400> SEQUENCE: 51
ggttggttgg atgaatatag ggga                                              24

<210> SEQ ID NO 52
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 52
ggtttctggg gtgac                                                        15

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
gtggtttctg gggtga                                                       16

<210> SEQ ID NO 54
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 54
gtggtttctg gggtgac                                                      17

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 55
guugauucuc agcccuucgc cc                                                22

<210> SEQ ID NO 56
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 56
sggcgaaggg gttggttgga tgaa                                              24

<210> SEQ ID NO 57
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 57
aatttaatac gactcactat agggagasgg cgaaggggtt ggttggatga a                51
```

<210> SEQ ID NO 58
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 58
acagggttga ttctcagccc ttcgccctcc cctatattca tccaaccaac cccttcgccs    60

<210> SEQ ID NO 59
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 59
ccggcggtgg tttctggggt gacagggttg attctcagcc cttcgccc                 48

<210> SEQ ID NO 60
<211> LENGTH: 100
<212> TYPE: DNA
<213> ORGANISM: Artificial Sequence
<220> FEATURE:
<223> OTHER INFORMATION: Synthetic Oligonucleotide

<400> SEQUENCE: 60
tatgctgccc gcgccaccgg ccggtcagcc gtctggccgt cgccgtgggc ggcgcagcgg    60
cggtgccggc ggtggtttct ggggtgacag ggttgattct                         100

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 61
tgcctatgct gcccgcgcca c                                              21

<210> SEQ ID NO 62
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 62
tgctgcccgc gcca                                                      14

<210> SEQ ID NO 63
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 63
tgcctatgct gcccgcgcca ccg                                            23

<210> SEQ ID NO 64
<211> LENGTH: 15
<212> TYPE: DNA
<213> ORGANISM: Artificial Sequence

```
<220> FEATURE:
<223> OTHER INFORMATION: Synthetic Oligonucleotide

<400> SEQUENCE: 64
tgctgcccgc gccac                                                    15

<210> SEQ ID NO 65
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 65
tgctgcccgc gccacc                                                   16

<210> SEQ ID NO 66
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 66
tgctgcccgc gccaccg                                                  17

<210> SEQ ID NO 67
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 67
ugauucucag cccuucgc                                                 18

<210> SEQ ID NO 68
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 68
agggttgatt ctcagcccttt cgccc                                        25

<210> SEQ ID NO 69
<211> LENGTH: 94
<212> TYPE: DNA
<213> ORGANISM: Artificial Sequence
<220> FEATURE:
<223> OTHER INFORMATION: Synthetic Oligonucleotide

<400> SEQUENCE: 69
gccggtcagc cgtctggccg tcgccgtggg cggcgcagcg gcggtgccgg cggtggtttc   60
tggggtgaca gggttgattc tcagcccttc gccc                               94

<210> SEQ ID NO 70
<211> LENGTH: 150
<212> TYPE: DNA
<213> ORGANISM: Artificial Sequence
<220> FEATURE:
<223> OTHER INFORMATION: Synthetic Oligonucleotide

<400> SEQUENCE: 70
```

```
tgcctatgct gcccgcgcca ccggccggtc agccgtctgg ccgtcgccgt gggcggcgca    60
gcggcggtgc cggcggtggt ttctggggtg acagggttga ttctcagccc ttcgccctcc   120
cctatattca tccaaccaac cccttcgccg                                    150
```

```
<210> SEQ ID NO 71
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 71
ugauugucag cccuucgc                                                  18

<210> SEQ ID NO 72
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 72
ugauugucag cccuucg                                                   17

<210> SEQ ID NO 73
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 73
aatttaatac gactcactat agggaga                                        27

<210> SEQ ID NO 74
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 74
accgccgcug cgccgcccac ggcgtttaaa aaaaaaaaaa aaaaaaaaaa aaaaaaa       57

<210> SEQ ID NO 75
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 75
accgccgcug cgccgcccac ggcg                                           24

<210> SEQ ID NO 76
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 76
```

```
agcggcgggg cgcugggccu ggucuuuaaa aaaaaaaaaa aaaaaaaaaa aaaaaaa      57

<210> SEQ ID NO 77
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 77
agcggcgggg cgcugggccu gguc                                          24

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 78
ccacaagcuu agaagauaga gagg                                          24

<210> SEQ ID NO 79
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 79
ctatcttcta agcttg                                                   16
```